US006924095B2

(12) United States Patent
McGrath et al.

(10) Patent No.: US 6,924,095 B2
(45) Date of Patent: Aug. 2, 2005

(54) RETROVIRUS ISOLATED FROM MANTLE HISTIOCYTES IN MANTLE CELL LYMPHOMA

(75) Inventors: Micahael S. McGrath, Burlingame, CA (US); Brian Herndier, Burlingame, CA (US)

(73) Assignee: The Regents of the University of California, Oakland, CA (US)

( * ) Notice: Subject to any disclaimer, the term of this patent is extended or adjusted under 35 U.S.C. 154(b) by 126 days.

(21) Appl. No.: 10/222,945

(22) Filed: Aug. 15, 2002

(65) Prior Publication Data

US 2003/0104009 A1 Jun. 5, 2003

Related U.S. Application Data

(60) Provisional application No. 60/312,686, filed on Aug. 15, 2001.

(51) Int. Cl.[7] .............................. C12Q 1/70; C12N 5/00; C12P 21/08; C07H 21/02; C07H 21/04
(52) U.S. Cl. ........................... 435/5; 435/6; 435/325; 435/810; 530/388.3; 530/389.1; 536/23.1; 536/23.72
(58) Field of Search ............................... 435/5, 6, 325, 435/810; 530/388.3, 389.1; 536/23.1, 23.72

(56) References Cited

U.S. PATENT DOCUMENTS 5,108,920 A 4/1992 Ng et al.
6,149,918 A 11/2000 McGrath et al.
6,242,201 B1 6/2001 Lane et al.

OTHER PUBLICATIONS

Boller, et al., "Characterization of the Antibody Response Specific for the Human Endogenous Retrovirus HTDV/HERV–K", J. of Virology (Jun. 1997) vol. 71(6) pp. 4581–4588.

Boller, et al., "Evidence that HERV–K is the Endogenous Retrovirus Sequence that Codes for the Human Tetatocarcinoma–Derived Retrovirus HTDV", Virology 196, 349–353 (1993).

Clerici, et al., "Immune Response to Antigens of Human Endogenous Retroviruses in Patients with Acute ir Stable Multiple Sclerosis", Journal of Neuroimmunology, 99, pp. 173–182 (1999).

Lower, et al., "The Viruses in all of us: Characteristics and Biological Significance of Human Endogenous Retrovirus Sequences", Proc. Natl. Acad. Sci. vol. 93 pp. 5177–5184 (May 1996).

Nelson, et al., "Molecular Investigations Implicate Human Endogenous Retroviruses as Mediators of Anti–Retroviral Antibodies in Autoimmune Rheumatic Disease", Immunological Investigations 28(4), 277–289 (1999).

Eugene D. Sverdlov, "Retroviruses and Primate Evolution", Bioassays 22: 161–171 (2000).

Tonjes, et al., "Genome–Wide Screening, Cloning, Chromosomal Assignment and Expression of Full–Length Human Endogenous Type K", Journal of Virology, vol. 73(11) pp. 9187–9195 (Nov. 1999).

Trabattoni, et al., "Augmented Type 1 Cytokines and Human Endogenous Retroviruses Specific Immune Responses in Patients with Acute Multiple Sclerosis", Journal of Neurovirology (2000) 6, Suppl 2, S38–S41.

(Continued)

Primary Examiner—Hankyel T. Park
(74) Attorney, Agent, or Firm—Carol L. Francis; Bozicevic, Field & Francis LLP

(57) ABSTRACT

The present invention features an isolated, intact virus associated with human lymphoma, and originally isolated from a mantle cell lymphoma, referred to herein as a mantle histiocyte retrovirus (MHRV). The invention also features compositions and methods for detecting MHRV, as well as methods and compositions for propagating MHRV in vitro, screening for anti-MHRV agents, and generation of attenuated MHRV strains.

58 Claims, 10 Drawing Sheets

OTHER PUBLICATIONS

Willer, et al., *"Two Groups of Endogenous MMTV Related Retroviral env Transcripts Expressed in Human Tissues"*, Virus Genes 15:2, 123–133 (1997).

Yolken, et al., *"Endogenous Retroviruses and Schizophrenia"*, Brain Research Reviews 31 (2000) 193–199.

McGrath, et al., *"Clonal HIV in the Pathogenesis of AIDS–Related Lymphoma"* Infectious Causes of Cancer: Targets for Intervention Chapter 13 pp. 231–242.

Michael Tristem, "Identification and Characterization of Novel Human Endogenous Retrovirus Families by Phylogenetic Screening of the Human Genome Mapping Project Database" Journal of Virology pp. 3715–3730 (Apr. 2000).

Accession No. AF164609 *Homo sapiens* endogenous retrovirus HERV–K101, complete sequence. Barbulescu et al., Molecular Genetics, (Jul. 2, 1999).

Accession No. AF164609, (Version AF164609.1) *Homo sapiens* endogenous retrovirus HERV–K101, complete sequence. Barbulescu et al., Molecular Genetics, (Jul. 2, 1999).

Accession No. M14123 Human endogenous . . . (Version M14123.1) Ono et al., Journal of Virology 60 (2), 589–598 (1986).

Accession No. AF164611 (Version AF164611.1) *Homo sapiens* endogenous retrovirus HERV–K103, complete sequence. Barbulescu et al., Molecular Genetics, (Jul. 2, 1999).

Accession No. AF164613 *Homo sapiens* endogenous retrovirus HERV–K107, long terminal repeat, complete sequence. Barbulescu et al., Molecular Genetics, (Jul. 2, 1999).

Accession No. AF164614 (Version AF164614.1) *Homo sapiens* endogenous retrovirus HERV–K108, complete sequence. Barbulescu et al., Molecular Genetics, (Jul. 2, 1999).

Accession No. AF164615 (Version AF164615.1) *Homo sapiens* endogenous retrovirus HERV–K109, complete sequence. Barbulescu et al., Molecular Genetics, (Jul. 2, 1999).

Accession No. P10265 Endogenous retrovirus HERV–K10, putative protease (Version M14123.1) Ono et al., Journal of Virology 60 (2), 589–598 (1986).

Accession No. Y10392 Human endogenous retrovirus HERV–K, gag, protease and Pol gene, Partial (Version Y10392.1) Tonjes et al., Virology 223 (2), 280–291 (1997).

Neto et al., "Shotgun Sequencing of the Human Transcriptome with ORF Expressed Sequence Tags," PNAS, vol. 97, No. 7, 3491–3496, Mar. 28, 2000.

Sugimoto et al., Transcriptionally Active HERV–K Genes: Identification, Isolation, and Chromosomal Mapping, Genomics 72, 137–144 (2001).

→ 1966 bp
→ 1321 bp

→ 304 bp marker  1  2  3    1  2  3
         \_____/    \_____/
            A          B A: AIDS-NHL DNA
B: MCL-A DNA          Tm = 65°C → 226 bp A: MHRV-Infected MO
B: Uninfected MO

FIG. 10

```
              1                                                          50
         LL   AGATCTAAAA GAAGACTGGA AAAGAATTGG CAAGGAACTA AAGCAGGTAG
         MT   AGATCTAAAA GAAGACTGGA AAAGAATTGG CAAGGAACTA AAGCAGGTAG
   S93-268102 AGATCTAAAA GAAGACTGGA AAAGAATTGG CAAGGAACTA AAGCAGGTAG
         UV   AGATCTAAAA GAAGACTGGA AAAGAATTGG CAAGGAACTA AAGCAGGTAG
     S92-4336 AGATCTAAAA GAAGACTGGA AAAGAATTGG CAAGGAACTA AAGCAGGTAG
         BR   AGATCTAAAA GAAGACTGGA AAAGAATTGG CAAGGAACTA AAGCAGGTAG 51                                                        100
         LL   GAAGGGTAAT ATCATTCCAC TTACAGTATG GAATGATTGG GCCATTATTA
         MT   GAAGGGTAAT ATCATTCCAC TTACAGTATG GAATGATTGG GCCATTATTA
   S93-268102 GAAGGGTAAT ATCATTCCAC TTACAGTATG GAATGATTGG GCCATTATTA
         UV   GAAGGGTAAT ATCATTCCAC TTACAGTATG GAATGATTGG GCCATTATTA
     S92-4336 GAAGGGTAAT ATCATTCCAC TTACAGTATG GAATGATTAG GCCATTATTA
         BR   GAAGGGTAAT ATCATTCCAC TTACAGTATG GAATGATTGG GCCATTATTA 101                                                       150
         LL   AAGCAGCTTT AGAACCATTT CAAAGAGAAG AAGATAGTGT TTCAGTTTCT
         MT   AAGCAGCTTT AGAACCATTT CAAAGAGAAG AAGATAGTGT TTCAGTTTCT
   S93-268102 AAGCAGCTTT AGAACCATTT CAAAGAGAAG AAGATAGTGT TTCAGTTTCT
         UV   AAGCAGCTTT AGAACCATTT CAAAGAGAAG AAGATAGTGT TTCAGTTTCT
     S92-4336 AAGCAGCTTT AGAACCATTT CAAAGAGAAG AAGATAGTGT TTCAGTTTCT
         BR   AAGCAGCTTT AGAACCATTT CAAAGAGAAG AAGATAGTGT TTCAGTTTCT 151                                                       200
         LL   GATGCCCCTG GAAGCTGTGT AATAGATTGT AAAGACAAGA CAGGGAAAAA
         MT   GATGCCCCTG GAAGCTGTGT AATAGATTGT AAAGACAAGA CAGGGAAAAA
   S93-268102 GATGCCCCTG GAAGCTGTGT AATAGATTGT AAAGACAAGA CAGGGAAAAA
         UV   GATGCCCCTG GAAGCTGTGT AATAGATTGT AAAGACAAGA CAGGGAAAAA
     S92-4336 GATGCCCCTG GAAGCTGTGT AATAGATTGT AAAGACAAGA CAGGGAAAAA
         BR   GATGCCCCTG GAAGCTGCGT AATAGATTGT AAAGACAAGA CAGGGAAAAA 201                                                       250
         LL   ATCCCAGAAA GAAACGGAAA GTTTACATTG CGAATATGTA GCAGAGCCAG
         MT   ATCCCAGAAA GAAACGGAAA GTTTACATTG CGAATATGTA GCAGAGCCAG
   S93-268102 ATCCCAGAAA GAAACGGAAA GTTTACATTG CGAATATGTA GCAGAGCCAG
         UV   ATCCCAGAAA GAAACGGAAA GTTTACATTG CAAATATGTA GCAGAGCCAG
     S92-4336 ATCCCAGAAA GAAACGGAAA GTTTACATTG CGAATATGTA GCAGAGCCAG
         BR   ATCCCAGAAA GAAACGGAAA GTTTACATTG CGAATATGTA GCAGAGCCAG 251                                                       300
         LL   TAATGGCTCA GTCAACGCAA AATGTTGACT ATAATCAATC AATTACAGGG
         MT   TAATGGCTCA GTCAACGCAA AATGTTGACT ATAATCAATC AATTACAGGG
   S93-268102 TAATGGCTCA GTCAACGCAA AATGTTGACT ATAATCAATC AATTACAGGG
         UV   TAATGGCTCA GTCAACGCAA AATGTTGACT ATAATCAATC AATTACAGGG
     S92-4336 TAATGGCTCA GTCAACGCAA AATGTTGACT ATAATCAATC AATTACAGGG
         BR   TAATGGCTCA GTCAACGCAA AATGTTGACT ATAATCAATC AATTACAGGG

301
         LL   GTTG  (SEQ ID NO: 7 )
         MT   GTTG  (SEQ ID NO: 7 )
   S93-268102 GTTG  (SEQ ID NO: 7 )
         UV   GTTG  (SEQ ID NO: 12 )
     S92-4336 GTTG  (SEQ ID NO: 13 )
         BR   GTTG  (SEQ ID NO: 14 )
```

RETROVIRUS ISOLATED FROM MANTLE HISTIOCYTES IN MANTLE CELL LYMPHOMA

STATEMENT REGARDING FEDERALLY SPONSORED RESEARCH

This invention was made with government support under grant nos. U01:CA 66529 and CA67381 awarded by the National Institutes of Health. The government may have certain rights in this invention.

FIELD OF THE INVENTION

The present invention relates to a human retrovirus, particularly to a human retrovirus isolated from a human, non-Hodgkins lymphoma, specifically a mantle cell lymphoma.

BACKGROUND OF THE INVENTION

As human beings age, they begin to develop a variety of chronic diseases the etiologies of which remain unclear at this time. These chronic diseases affect virtually all organ systems of the body. Several animal models of chronic disease involve viral infection, especially retroviral infection. For example, murine leukemia viruses have been implicated in causing lymphoma, autoimmune and immunodeficiency diseases. The study of these types of animal models suggested that retroviruses play significant roles in those disease states. However, the extrapolation of findings within animal models to humans have not proven very successful in the identification of fully infectious retroviruses associated with chronic immunologic diseases outside of HTLV (with lymphoma), HIV (with AIDS), and HuLAV (with human B-cell, non-Hodgkins lymphoma (U.S. Pat. No. 5,108,920).

In searching for potential agents associated with other chronic diseases a vast array of human endogenous retroviral elements were discovered and characterized (Lower et al. *Proc Natl Acad Sci* 93:5177–5184 (1996); Tonjes et al. *J Virol* 73(11):9187–9195 (1999); Sverdlov *Bioessays* 22(2):161–171 (2000)). The closest class of endogenous retroviral element identified in humans to those associated with chronic disease in mouse disease models are the human endogenous retroviruses (HERV) (Wilier et al. *Virus Genes* 15(2):123–133 (1997)). Evidence for expression of HERV related genes or antibodies to HERV elements have been identified in a variety of chronic diseases such as terato carcinoma (Boller et al. *J Virol* 71:4581–4588 (1997); Boller et al. *Virology* 196:349–353 (1993)), lymphoma (Lower et al., (1996) supra), multiple sclerosis (Clerici et al. *J Neuroimmunol* 99(2):173–182 (1999); Trabattoni et al. *J Neurovirol* 6(Suppl 2):S38–41 (2000)), autoimmune rheumatic diseases (Nelson et al. *Immunol Invest* 28(4):277–289 (1999)), and most recently schizophrenia (Yolken et al. *Brain Res Rev* 31(2–3):193–199 (2000)). However, as human endogenous retroviral elements make up almost 1% of the human genome and each of these elements is highly related to other endogenous elements, their role in the pathogenesis of disease has been difficult to assess.

Despite the advances in identification of retroviruses and other agents associated with disease, identification of the causative or associated agents of many diseases remains elusive. Certain types of lymphoid malignancies are among such diseases. Three major categories of lymphoid malignancies have been recognized based on morphology and cell lineage: B-cell neoplasms, T-cell/natural killer (NK)-cell neoplasms, and Hodgkins lymphoma. B-cell and T-cell/NK neoplasms are often referred to as non-Hodgkins lymphomas. Both lymphomas and lymphoid leukemias are included in within these classifications because both solid and circulating phases are present in many lymphoid neoplasms. Within the B- and T-cell categories, two subdivisions are recognized: precursor neoplasms, which correspond to the earliest stages of differentiation, and more mature differentiated neoplasms. The aggressive lymphomas are particularly difficult to diagnose at an early stage, largely due to their primarily asymptomatic nature. Thus, diagnosis of the aggressive non-Hodgkins lymphomas is normally at a stage late in the course of disease, and the prognosis is normally poor.

Mantle cell lymphoma is an example of an aggressive, non-Hodgkins lymphoma. Mantle cell lymphoma is found in lymph nodes, the spleen, bone marrow, blood, and sometimes the gastrointestinal system (lymphomatous polyposis). Mantle cell lymphoma is generally characterized by CD5-positive follicular mantle B cells, a translocation of chromosomes 11 and 14, and an overexpression of the cyclin D1 protein. Like the low-grade lymphomas, mantle cell lymphoma appears incurable with anthracycline-based chemotherapy and occurs in older patients with generally asymptomatic advanced-stage disease. However, the median survival is significantly shorter (3–5 years) than that of other lymphomas; hence this histology is now considered to be an aggressive lymphoma. A diffuse pattern and the blastoid variant have an aggressive course with shorter survival, while the mantle zone type may have a more indolent course. It is unclear which chemotherapeutic approach offers the best long-term survival in this clinicopathologic entity; refractoriness to chemotherapy is a usual feature. Many investigators are exploring high-dose therapy with stem cell/marrow support or the use of interferon or anti-CD20 antibodies after CHOP (cyclophosphamide, doxorubicin, vincristine, prednisone) chemotherapy.

Identification of agents of chronic disease such as cancer are important, not only for diagnosis of affected patients and development of anti-cancer drugs, but also in the prevention of the spread of chronic disease where causative agent is transmissible, e.g., through blood transfusion, transplant of infected tissues, sharing or re-use of needles, sexual contact, and the like. Transmission of lymphoma from a donor to a recipient can occur due to direct infection with the virus.

There is a need in the field for identification of agents that are associated with (and thus can serve as a marker for) or cause cancers of unknown etiology. Furthermore, identification of agents associated with chronic diseases, such as cancer, allow for screening of biological materials for the associated agent prior to use (e.g., screening of blood, blood products, tissues, and the like). The present invention addresses this need.

SUMMARY OF THE INVENTION

The present invention features an isolated, intact virus associated with human lymphoma, and originally isolated from a mantle cell lymphoma, referred to herein as a mantle histiocyte retrovirus (MHRV). The invention also features compositions and methods for detecting MHRV, as well as methods and compositions for propagating MHRV in vitro, screening for anti-MHRV agents, and generation of attenuated MHRV strains.

In one aspect the invention features, an isolated mantle histiocyte retrovirus (MHRV) particle. In specific embodiments, the MHRV particle comprises an RNA genome encoding a GAG polypeptide comprising an amino acid sequence of amino acid residues 1–22 of SEQ ID NO:8. In other specific embodiment, the MHRV particle comprises an RNA genome characterized in that PCR amplification using a first primer comprising SEQ ID NO:2 and a second primer comprising SEQ ID NO:3 produces an amplification product of about 304 bp, which amplification product may comprise the sequence of SEQ ID NO:1. In still further specific embodiments, the MHRV particle contains an RNA genome that, following infection and activity of viral reverse transcriptase, generates a cDNA that hybridizes under conditions of high stringency to a nucleic acid sequence of SEQ ID NO:1. In another embodiment, the MHRV viral particle comprises an RNA molecule comprising a sequence corresponding to SEQ ID NO:1. In still another embodiment, the MHRV particle is characterized by being isolatable from a human lymphoma; having a particle diameter of from about 90 nm to 110 nm; having a membrane lipid bilayer; having an RNA genome visible by electron microscopy as a conical eccentric nucleoid; and having a GAG envelope polypeptide comprising amino acid residues 1–22 of the amino acid sequence of SEQ ID NO:8 or, alternatively or in addition, having an RNA genome comprising a nucleic acid sequence corresponding to nucleotide residues 1–66 of SEQ ID NO:7.

In related aspects, the invention features an isolated mammalian cell (e.g., a macrophage) infected with an MHRV viral particle. Optionally, the infected cell produces MHRV particles.

In another aspect, the invention features an isolated polynucleotide (referred to herein without limitation as an MHRV polynucleotide) comprising a sequence encoding a polypeptide comprising an amino acid sequence of at least 4 contiguous amino acid residues of amino acid residues 1–22 of SEQ ID NO:8. In related aspects, the invention features an isolated MHRV polynucleotide comprising a sequence of at least 12 contiguous residues of nucleic acid residues 1–66 of SEQ ID NO:7; an isolated polynucleotide comprising a sequence that hybridizes under conditions of high stringency to at least a portion of the polynucleotide sequence of nucleotides 1–66 of SEQ ID NO:7; an isolated polynucleotide comprising a sequence having at least 65% identity to at least 12 contiguous nucleotides of nucleic acid residues 1–66 of SEQ ID NO:7.

In related aspects, the invention features an isolated recombinant host cells and isolated vectors containing the polynucleotide of the invention.

In another aspect, the invention features an isolated MHRV GAG polypeptide. In related aspects, the isolated polypeptide is encoded by an MHRV GAG polynucleotide as described above. In further related aspects, the invention features an isolated antibody that specifically binds an isolated MHRV GAG polypeptide.

In another aspect the invention features a method for detecting MHRV by contacting a biological sample suspected of containing MHRV with an MHRV-specific probe for a time sufficient for binding of the MHRV-specific probe to the sample to form complexes between the probe and a probe target; and detecting complexes of the MHRV-specific probe and the probe target in the sample. Detection of complexes in the sample indicates MHRV is present in the sample.

In specific embodiments of the MHRV detection methods above, the probe target is nucleic acid, and the MHRV-specific probe is a nucleic acid and comprises at least 8 contiguous nucleotide residues of SEQ ID NO:1; or at least 8 contiguous nucleotide residues of residues 1–66 of SEQ ID NO:7. In other embodiments, the MHRV-specific probe is an MHRV-specific antibody and the probe target is an MHRV GAG polypeptide. In still other embodiments, the probe target is an anti-MHRV antibody and the MHRV-specific probe is a polypeptide comprising amino acid residues 1–22 of SEQ ID NO:8. In related embodiments, the biological sample is blood, a blood-derived product, plasma, serum, or tissue containing a macrophage or a macrophage-derived tumor cell.

In another aspect, the invention features a method for detecting MHRV in a sample comprising: contacting a biological sample suspected of containing MHRV with a first MHRV-specific nucleic acid probe and with a second MHRV-specific nucleic acid probe, wherein the first probe and the second probe each comprise at least 15 contiguous nucleotides of a nucleic acid sequence of SEQ ID NO:7 or complement thereof, and where contacting is under conditions effective to produce an amplified DNA product; and detecting the amplified DNA product. Detection of amplified DNA product corresponding to an amplified DNA product expected from a nucleic acid sequence comprising SEQ ID NO:7 indicates the MHRV is present in the sample.

In specific embodiments of the MHRV detection methods of the invention, the first probe comprises a sequence selected from the group consisting of HERV-9 and HERV-10. In other specific embodiments; the second probe comprises a sequence selected from the group consisting of HERV-8, HERV-11, and HERV-12. In still other embodiments, the first probe is HERV-8, the second probe is HERV-9, wherein detection of an amplified product of about 304 bp indicates MHRV is in the sample; the first probe is HERV-9 the second probe is HERV-12, wherein detection of an amplified product of about 1321 bp indicates MHRV is in the sample; or the first probe is HERV-10 the second probe is HERV-11, wherein detection of an amplified product of about 1966 bp indicates MHRV is in the sample.

In another aspect the invention features a kit for detection of mantle histiocyte retrovirus (MHRV), the kit comprising an MHRV-specific probe, wherein the probe is an MHRV-specific nucleic acid probe that specifically hybridizes to a sequence encoding an MHRV GAG polypeptide; an MHRV-specific GAG antibody; or n MHRV polypeptide that specifically binds an anti-MHRV GAG polypeptide.

In another aspect, the invention features a method of screening for anti-MHRV antiviral agents, the method comprising: contacting a candidate agent with a culture comprising a mammalian cell infected with MHRV, which cell produces viral particles; and detecting MHRV viral particles in supernatant of the culture. Detection of a decrease in MHRV viral particles in the supernatant indicates that the candidate agent as activity as an anti-MHRV antiviral agent.

In still another aspect the invention features a method for detecting an MHRV-associated disease, the method comprising: contacting a biological sample with an MHRV-specific probe, wherein the biological sample was obtained from a subject suspected of having an MHRV-associated disease, said contacting being for a time sufficient for binding of the MHRV-specific probe to the sample to form complexes between the probe and a probe target; and detecting complexes of the MHRV-specific probe and the probe target in the sample. Detection of complexes in the sample indicates MHRV is present in the sample, and that the subject may have an MHRV-associated disease. In related embodiments, the MHRV-associated disease is an MHRV-associated lymphoma, teratocarcinoma, multiple sclerosis, autoimmune rheumatic diseases, or schizophrenia.

In another aspect the invention features a method for producing an MHRV GAG polypeptide, the method comprising the steps of culturing a recombinant host cell containing a recombinant MHRV GAG polypeptide-encoding polynucleotide sequence under conditions suitable for the expression of the polypeptide; and recovering the polypeptide from the host cell culture.

In another aspect the invention features an immunogenic composition comprising an immunogenic polypeptide, wherein the immunogenic polypeptide comprises an amino acid sequence of amino acid residues 1–22 of a GAG polypeptide of mantle histiocyte retrovirus (MHRV).

In another aspect the invention features an immunogenic composition comprising a nucleic acid molecule having a sequence encoding an immunogenic polypeptide, wherein the immunogenic polypeptides comprises an amino acid sequence of amino acid residues 1–22 of a GAG polypeptide of mantle histiocyte retrovirus (MHRV), and wherein the nucleic acid sequence is adapted for expression in a mammalian cell.

In another aspect, the invention features an isolated recombinant MHRV vector comprising a viral genome comprising an MHRV polynucleotide (e.g., a polynucleotide encoding at least 4 contiguous amino acid residues of 1–22 of SEQ ID NO:8), at least one restriction site suitable for insertion of a heterologous nucleic acid, and a nucleic acid of interest comprising a sequence heterologous to the MHRV polynucleotide, wherein the nucleic acid is operably inserted for expression in a host upon introduction of the MHRV vector into the host cell. In specific embodiments, the restriction site is non-naturally occurring in the MHRV genome.

In another aspect, the invention features an isolated recombinant MHRV particle comprising a recombinant MHRV genome comprising an MHRV polynucleotide (e.g., a polynucleotide encoding at least 4 contiguous amino acid residues of 1–22 of SEQ ID NO:8), and at least one restriction site suitable for insertion of a heterologous nucleic acid. In specific embodiments, the recombinant MHRV particle comprises a nucleic acid having a sequence heterologous to the MHRV polynucleotide, wherein the nucleic acid is operably inserted for expression in a host upon introduction of the MHRV vector into the host cell. In other specific embodiments, the MHRV particle is replication-defective or replication competent.

BRIEF DESCRIPTIONS OF THE DRAWINGS

FIG. 1 is a schematic showing the arrangement of the MHRV genome, as well as the regions of homology to HERV-K109, the relative positions of primers used to amplify the MHRV GAG-encoding region, and the sequences of the primers and the amplified 304 bp PCR product generated using the HERV-8 and HERV-9 primers. Numbers along the schematics showing the MHRV genomic arrangement and the regions of homology refer to corresponding nucleotide residue positions in the MHRV genome.

Figure 7:
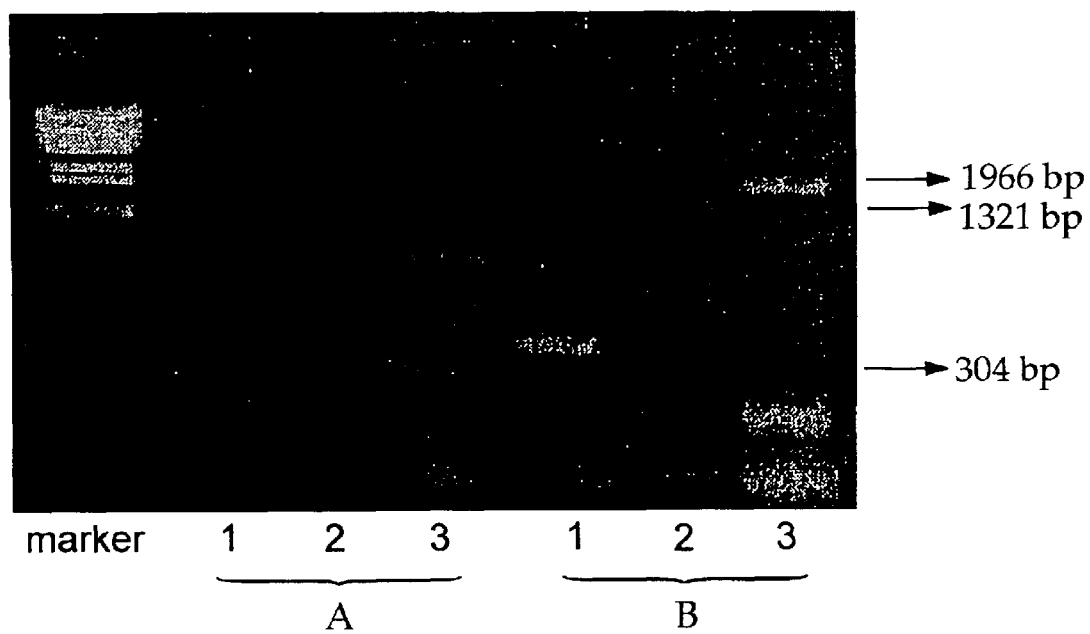

FIG. 7 is a photograph showing the results of PCR amplification using MHRV GAG-specific primers and nucleic acid from an AIDS-Non-Hodgkin's lymphoma (AIDS-NHL) and the original mantle cell lymphoma DNA (MCL-1) as a positive control. A=AIDS-NHL DNA; B=MCL-1 DNA.

Figure 8:
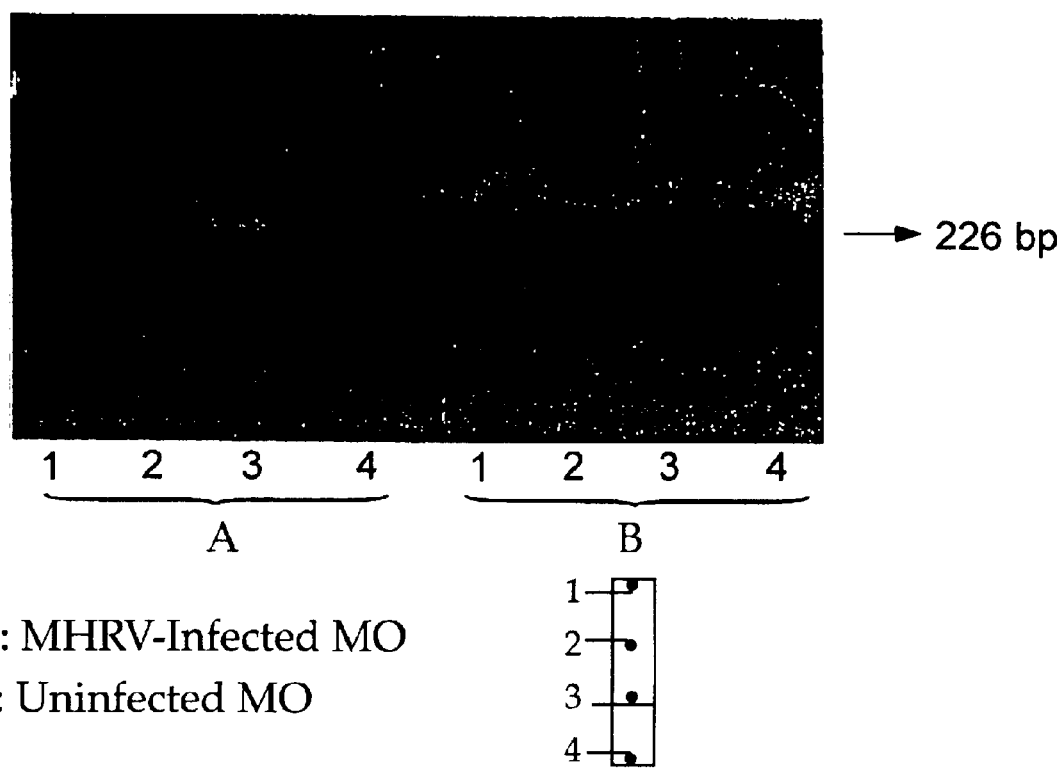

FIG. 8 is a photograph showing the results of PCR amplification using MHRV GAG-specific primers on RNA isolated from a primary macrophage culture infected with isolated MHRV particles.

Figure 9:
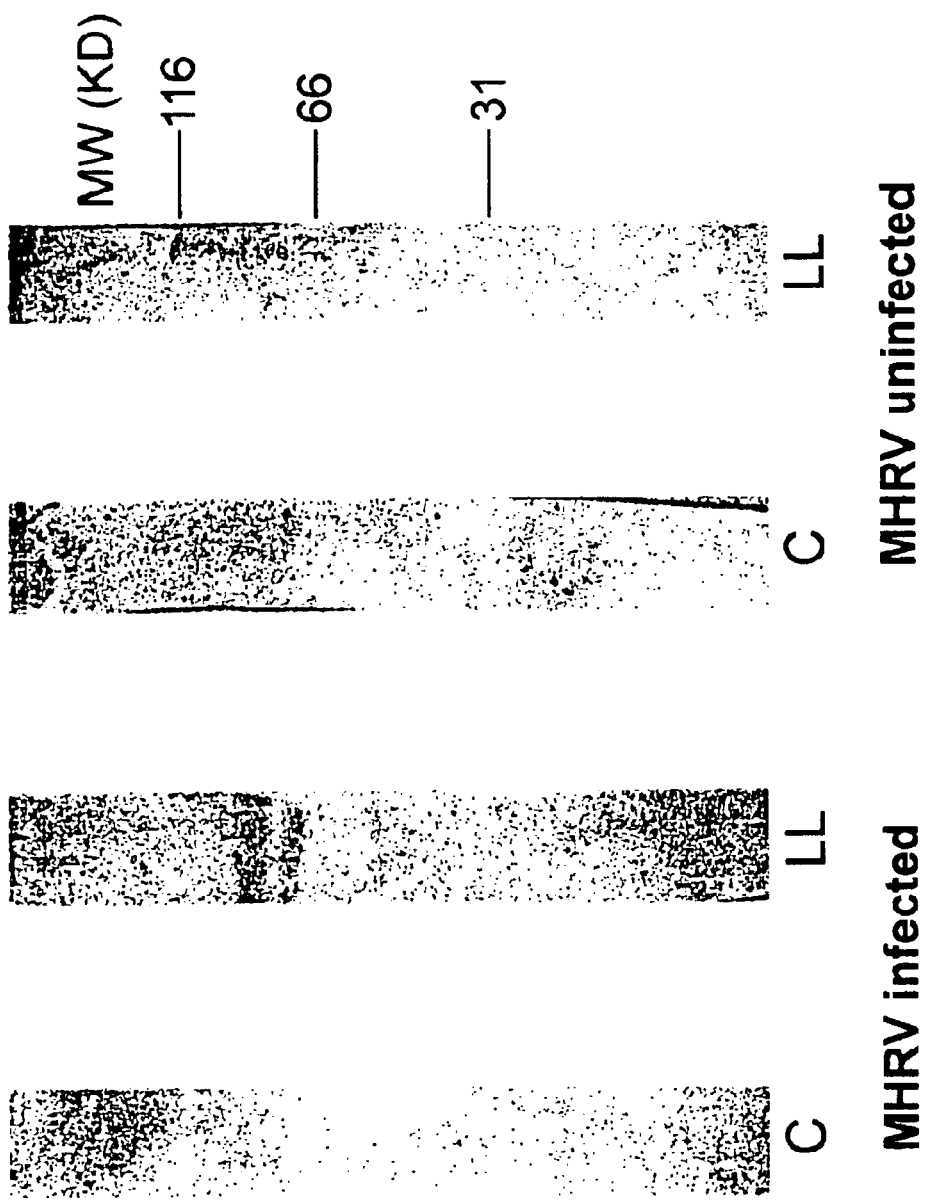

FIG. 9 is a Western blot of MHRV-infected and MHRV-uninfected cells without (C=control) and with (LL) plasma antibody from an MHRV-infected patient. Anti-IgG-AP antibody was used to detect plasma antibody binding.

FIG. 10 is an alignment of DNA sequences of PCR products (SEQ ID NO:12–14) generated from different lymphomas within the 304 bp MHRV gag segment.

DETAILED DESCRIPTION OF THE INVENTION

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a viral particle" includes a plurality of such viral particles and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

"Mantle histiocyte retrovirus" (MHRV) as used herein is meant to refer to a human retrovirus described herein, which can be generally characterized by any one or more of the following characteristics: 1) being isolatable from a human mantle cell lymphoma (as described herein); 2) virion particles of about 90 nm to 110 nm in diameter as observed by electron microscopy; 3) having a membrane lipid bilayer; 4) a conical eccentric nucleoid containing an RNA genome. At the protein level, MHRV is characterized in that the viral particle has a GAG core polypeptide comprising amino acid residues 1–22 of the amino acid sequence of SEQ ID NO:8. At the nucleic acid sequence level, MHRV is characterized in that the RNA genome comprises a nucleic acid sequence corresponding to nucleotide residues 1–66 of SEQ ID NO:7, which is a portion of a GAG-encoding sequence that is unique to MHRV. By "corresponding to nucleotide residues" in this context is meant that the RNA has the sequence of the provided DNA sequence, except that the deoxyribonucleotides thymine (T) is replaced with ribonucleotide uracil (U). It is noted that reference to MHRV as being isolated from a human mantle cell lymphoma is not intended to limit the definition to only MHRV isolated from this source, but is rather only a means of isolating and describing the virus of the invention.

By "isolated viral nucleic acid" or "isolated viral polypeptide" is meant that the MHRV viral protein or peptide provided by the invention is at least 60%, by weight, free from the proteins and naturally-occurring organic molecules with which it is naturally associated. Preferably, the preparation is at least 75%, more preferably at least 90%, and most preferably at least 99%, by weight, MHRV polypeptide. An isolated viral protein or peptide may be obtained, for example, by extraction from an MHRV virus particle, which can be obtained from a macrophage of a human mantle cell lymphoma,; by expression of a recombinant nucleic acid encoding an MHRV viral protein or peptide; or by chemically synthesizing the protein or peptide. Purity can be measured by any appropriate method, e.g., column chromatography, polyacrylamide gel electrophoresis, or HPLC analysis.

The terms "polynucleotide" and "nucleic acid", used interchangeably herein, refer to a polymeric forms of nucleotides of any length, either ribonucleotides or deoxynucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. These comprise intronic and exonic sequences (see, e.g., Niwa et al. (1999) Cell 99(7):691–702).

The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. Peyrottes et al. (1996) Nucl. Acids Res. 24:1841–1848; Chaturvedi et al. (1996) Nucl. Acids Res. 24:2318–2323. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a support (e.g., to a solid or semi-solid support, to a support for use as an array, and the liked). Polynucleotides can be provided in a variety of forms, e.g., associated with an array or provided as part of a library of polynucleotides (e.g., a library of vectors containing polynucleotides of interest, a library of recombinant host cells containing such vectors, and the like).

It is understood that reference to DNA in the context of the RNA virus MHRV, and other RNA viruses, is meant to refer to a DNA sequence as it would be produced from the genomic RNA, without limitation as to the method of making the DNA sequence. Similarly, its is understood that DNA sequences of MHRV sequences, and other RNA viruses, encompasses the corresponding RNA, where uracil (U) is substituted for thymine (T), and further encompasses the complementary strand and its corresponding RNA sequence.

The terms "polypeptide" and "protein", used interchangeably herein, refer to a polymeric form of amino acids of any length, which can include coded and non-coded amino acids, chemically or biochemically modified (e.g., post-translational modification such as glycosylation) or derivatized amino acids, polymeric polypeptides, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. Polypeptides can also be modified to, for example, facilitate attachment to a support (e.g., to a solid or semi-solid support, to a support for use as an array, and the liked).

As used herein, a polynucleotide "derived from" a designated sequence refers to a polynucleotide sequence which is comprised of a sequence of approximately at least about 6 contiguous nucleotides, at least about 8 nucleotides, at least about 10–12 contiguous nucleotides, and at least about 15–20 contiguous nucleotides corresponding to a region of the designated nucleotide sequence. "Corresponding" means homologous to or complementary to the designated sequence. Preferably, the sequence of the region from which the polynucleotide is derived is homologous to or complementary to a sequence which is unique to an MHRV genome.

Whether or not a sequence is unique to the MHRV genome can be determined by techniques known to those of skill in the art. For example, the sequence can be compared to sequences in databanks, e.g., GenBank, to determine whether it is present in the uninfected host or other organisms. The sequence can also be compared to the known sequences of other viral agents, including other retroviruses, particularly human endogenous retroviruses. and to members of Retroviridae. The correspondence or non-correspondence of the derived sequence to other sequences can also be determined by hybridization under the appropriate stringency conditions. Hybridization techniques for determining the complementarity of nucleic acid sequences are known in the art, and are discussed infra. See also, for example, Maniatis et al. (1982). In addition, mismatches of duplex polynucleotides formed by hybridization can be determined by known techniques, including for example, digestion with a nuclease such as S1 that specifically digests single-stranded areas in duplex polynucleotides. Regions from which typical DNA sequences may be "derived" include but are not limited to, for example, regions encoding specific epitopes, as well as non-transcribed and/or non-translated regions.

The derived polynucleotide is not necessarily physically derived from the nucleotide sequence shown, but may be generated in any manner, including for example, chemical synthesis or DNA replication or reverse transcription or transcription. In addition, combinations of regions corresponding to that of the designated sequence may be modified in ways known in the art to be formulated with an intended use.

Similarly, a polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 contiguous amino acids, and more preferably at least 8–10 contiguous amino acids, and even more preferably at least 11–15 contiguous amino acids, or which is immunologically identifiable with a polypeptide encoded in the sequence. This terminology also includes a polypeptide expressed from a designated nucleic acid sequence.

A recombinant or derived polypeptide is not necessarily translated from a designated nucleic acid sequence, for example, the sequence encoding MHRV GAG polypeptide as set forth in SEQ ID NO:7, or from an MHRV genome; it may be generated in any manner, including for example, chemical synthesis, or expression of a recombinant expression system, or isolation from MHRV, including mutated MHRV. A recombinant or derived polypeptide may include one or more analogs of amino acids or unnatural amino acids in its sequence. Methods of inserting analogs of amino acids into a sequence are known in the art. It also may include one or more labels, which are known to those of skill in the art.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, and recombinant polynucleotide sequences.

By "heterologous", as used in, for example, the phrase "promoter element heterologous to a MHRV GAG polynucleotide" is meant that the two elements joined are not normally found joined together in nature, e.g., are from different sources (e.g., the promoter element is not joined to the polynucleotide encoding an MHRV GAG polypeptide found in nature).

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

By "specifically binds" as used in the context of an MHRV polynucleotide (e.g., nucleic acid probe) or polypeptide (e.g., as detected using an antibody that specifically binds the polypeptide) means that the MHRV polynucleotide or polypeptide can be used as a marker for MHRV so that MHRV is detected so as to be distinguished from non-MHRV polynucleotides or non-MHRV polypeptides. For example, a specific MHRV polynucleotide is one that can be used to specifically detect MHRV nucleic acid (in, e.g., nucleic acid amplification- or hybridization-based assays) so as to differentiate MHRV nucleic acid from non-MHRV nucleic acid. Similarly, a specific MHRV polypeptide is a polypeptide that can be detected (e.g., by antibody-based assay) so as to specifically detect MHRV in a sample and differentiate MHRV polypeptide from non-MHRV polypeptides. Similarly, an MHRV-specific antibody is an antibody that can be used in detection of an MHRV-specific polypeptide or MHRV-specific epitope so as to specifically detect MHRV in a sample and differentiate MHRV polypeptide from non-MHRV polypeptides.

"MHRV marker" as used herein is meant to refer to a biological molecule that can be detected in a sample, and which indicates the presence, or prior presence (e.g., prior exposure), of the source of the sample to MHRV. Exemplary MHRV markers include MHRV viral particles, MHRV nucleic acid that are specific for MHRV, MHRV polypeptides that are specific for MHRV, and anti-MHRV antibodies.

"Biological samples", particularly as used in the context of detection of MHRV, refers to any biological material obtained from a subject, generally a human subject. Such material includes, but is not necessarily limited to, a sample of tissue or fluid isolated from an individual, including but not limited to, for example, blood, blood-derived products, plasma, serum, spinal fluid, lymph fluid, the external sections of the skin, respiratory, intestinal, and genitourinary tracts, tears, saliva, milk, blood cells, cells (e.g., macrophages, bone marrow, cancerous cells of a lymphoma, tumor cells, pre-cancerous cells (e.g., dysplastic cells), and the like), tumors, organs, and also samples of in vitro cell culture constituents (including but not limited to conditioned medium resulting from the growth of cells in cell culture medium, putatively virally infected cells, recombinant cells, and cell components).

"Subjects" or "patients" as used herein is meant to encompass any subject or patient amenable to application of the methods of the invention, e.g., diagnostic methods. Mammalian subjects and patients, particularly human subjects or patients are of particular interest.

As used herein, the terms "macrophage" and "monocyte" are used interchangeably, as it is understood that in the art the term "monocyte" is often used to describe a circulating mononuclear cell that expresses the CD14 cell surface marker, and when in a tissue this cell is also classified as a macrophage.

A "proliferating macrophage" is a term understood in the art and as used herein denotes a macrophage which is dividing. Normally a macrophage is a terminally differentiated cell incapable of further division. For purposes of this invention, a "proliferating macrophage" is capable of further division or is in a portion of the cell cycle not considered to be terminal or end stage. Proliferation may be clonal, i.e., is derived from a single cell.

As used herein, detecting the "presence of proliferating macrophages" generally means detecting the level of proliferating macrophages. It is understood that an absolute or even relative level need not be determined; an observation of detectable proliferating macrophages is sufficient.

"Microarray" and "array," as used interchangeably herein, comprise a surface with an array, preferably ordered array, of putative binding (e.g., by hybridization) sites for a biochemical sample (target) which often has undetermined characteristics. In a preferred embodiment, a microarray refers to an assembly of distinct polynucleotide or oligonucleotide probes immobilized at defined positions on a substrate. Arrays are formed on substrates fabricated with materials such as paper, glass, plastic (e.g., polypropylene, nylon), polyacrylamide, nitrocellulose, silicon, optical fiber or any other suitable solid or semi-solid support, and configured in a planar (e.g., glass plates, silicon chips) or three-dimensional (e.g., pins, fibers, beads, particles, microtiter wells, capillaries) configuration.

Probes forming the arrays may be attached to the substrate by any number of ways including (i) in situ synthesis (e.g., high-density oligonucleotide arrays) using photolithographic techniques (see, Fodor et al., *Science* (1991), 251:767–773; Pease et al., *Proc. Natl. Acad. Sci. U.S.A.* (1994), 91:5022–5026; Lockhart et al., *Nature Biotechnology* (1996), 14:1675; U.S. Pat. Nos. 5,578,832; 5,556,752; and 5,510,270); (ii) spotting/printing at medium to low-density (e.g., cDNA probes) on glass, nylon or nitrocellulose (Schena et al, *Science* (1995), 270:467–470, DeRisi et al, *Nature Genetics* (1996), 14:457–460; Shalon et al., *Genome Res.* (1996), 6:639–645; and Schena et al., *Proc. Natl. Acad. Sci. U.S.A.* (1995), 93:10539–11286); (iii) by masking (Maskos and Southern, *Nuc. Acids. Res.* (1992), 20:1679–1684) and (iv) by dot-blotting on a nylon or nitrocellulose hybridization membrane (see, e.g., Sambrook et al., Eds., 1989, Molecular Cloning: A Laboratory Manual, 2nd ed., Vol. 1–3, Cold Spring Harbor Laboratory (Cold Spring Harbor, N.Y.)). Probes may also be noncovalently immobilized on the substrate by hybridization to anchors, by means of magnetic beads, or in a fluid phase such as in microtiter wells or capillaries. The probe molecules are generally nucleic acids such as DNA, RNA, PNA, and cDNA but may also include proteins, polypeptides, oligosaccharides, cells, tissues and any permutations thereof which can specifically bind the target molecules.

"Treatment" as used herein refers to prophylaxis and/or therapy.

As used herein, "purified MHRV" refers to a preparation that is enriched for MHRV, or a preparation having isolated MHRV, which preparation has been obtained from the cellular constituents with which the virus is normally associated, and from other types of viruses which may be present in the infected tissue. The techniques for isolating viruses are known to those of skill in the art, and include, for example, centrifugation, affinity chromatography, and the like.

The term "MHRV particle" as used herein include entire virion as well as particles which may be intermediates in virion formation. MHRV particles generally have one or more MHRV polypeptides associated with MHRV nucleic acid.

As used herein, the term "probe" refers to a molecule useful in specific detection of MHRV. "Probes" thus include, a polynucleotide that specifically hybridizes to an MHRV polynucleotide in a target region, due to complementarity of at least one sequence in the probe with a sequence in the target region. Unless specifically noted otherwise, probes encompass primers (e.g., primers used in PCR-based amplification of a region adjacent a target region). "Probes" also include antibodies that specifically bind an MHRV polypeptide, as well as MHRV polypeptides that specifically bind anti-MHRV antibodies. The meaning of probe will be readily apparent to the ordinarily skilled artisan from the context of the use of the term.

An "MHRV-specific probe" is a molecule (e.g., nucleic acid, antibody, polypeptide) that specifically binds an MHRV-specific probe target. Exemplary MHRV-specific probes include nucleic acid that specifically hybridizes to a unique sequence of MHRV, nucleic acid primer pairs that facilitate amplification of an MHRV-specific nucleic acid sequence; an anti-MHRV GAG polypeptide that specifically binds the GAG of MHRV, and an MHRV GAG polypeptide that specifically binds an anti-MHRV GAG antibody.

As used herein, the term "target region" as used in the context of a nucleic acid probe refers to a region of the nucleic acid which is to be amplified and/or detected. "Target region" as used in the context of antibody-polypeptide (antibody-antigen) complex formation refers to a region of the polypeptide that forms the epitope specifically bound by the antibody.

"Probe target" as used herein is meant to refer to a molecule to which an MHRV-specific probe specifically binds. The probe target can be nucleic acid (RNA or DNA), an antibody, or a polypeptide. Combinations of probes and probe targets described herein will be readily apparent to one of ordinary skill in the art upon reading the present specification.

As used herein, the term "viral nucleic acid", which includes MHRV nucleic acid, refers to nucleic acid from the viral genome, fragments thereof, transcripts thereof, and mutant sequences derived therefrom. Viral nucleic acid can be derived from any source, e.g., cells, synthetic production techniques, recombinant expression techniques, and the like.

By "MHRV-associated disease" is meant a disease associated with cells having genomically integrated MHRV nucleic acid. MHRV-associated lymphomas are an example of such MHRV-associated diseases.

By "MHRV-associated lymphoma" is meant a lymphoma having cells in which MHRV nucleic acid is genomically integrated. The lymphoma may be one which has MHRV as its primary causative agent, or one in which MHRV is commonly found or associated, but which is not primarily caused by MHRV.

"Recombinant host cells", "host cells", "cells", "cell lines", "cell cultures", and other such terms denoting microorganisms or higher eukaryotic cells cultured as unicellular entities refer to cells which can be, or have been, used as recipients for recombinant vector or other transfer DNA, and include the progeny of the original cell which has been transfected. It is understood that the progeny of a single parental cell may not necessarily be completely identical in morphology or in genomic or total DNA complement as the original parent, due to natural, accidental, or deliberate mutation.

OVERVIEW

The present invention is based on the discovery of a novel retrovirus, referred to herein as mantle histiocyte retrovirus (MHRV). MHRV is associated with human lymphoma, and is the first replication competent human retrovirus having significant elements shared with a human endogenous retrovirus (HERV), specifically HERV-K109. The virus of the invention was initially isolated from macrophages of a mantle cell lymphoma, and thus was named MHRV to reflect such. However, the inventors have detected MHRV in other lymphomas, including AIDS large cell lymphoma and non-AIDS follicular lymphoma. Thus, the name MHRV is not intended to be limiting, as these findings indicate that MHRV is associated with human cancers such as lymphomas, inclusive of mantle cell lymphoma.

MHRV is transmissible and can cause lymphoma in the recipient as demonstrated by the ability of cells from which MHRV was isolated to produce lymphoma in an animal model. In view of such, the invention also provides methods and compositions for detection of MHRV in biological samples, which can be used in the context of diagnosis as well as in prevention (e.g., in screening of blood, blood products, and tissues prior to transfer to a recipient).

Various aspects of the invention will now be described in more detail.

Mantle Histiocyte Retrovirus (MHRV)

Mantle histiocyte retrovirus (abbreviated herein as MHRV) was originally isolated from a human mantle cell lymphoma. MHRV particles are approximately 90 nm to 1110 nm in diameter as observed by electron microscopy, and have a membrane lipid bilayer encapsulating a conical eccentric nucleoid containing the RNA genome. Retroviral morphology observed was of the B/D-type. The regions of the MHRV genome corresponding to the 5'LTR (long terminal repeat), pro, poly, env, and 3'LTR regions share approximately 98–100% homology with the human endogenous retrovirus (HERV) designated HERV-K109 (see FIG. 1). The gag region of MHRV is, by contrast, only 93% homologous to the gag of HERV-K109. This observation suggests the MHRV is a result of a recombination event with HERV-K109 and another exogenous virus. As a result, the region of the MHRV genome extending from about nucleotide residue 1246 to about nucleic residue 3445, the region corresponding to the GAG-encoding sequence, as well as the GAG polypeptide itself, serve as markers for MHRV.

The invention also encompasses methods for identifying macrophage-tropic viruses such as MHRV. In general, these methods are based upon the methods that led to the identification of MHRV, which are described in detail in the Examples section below. For example, tissues are first identified by histologic inspection as having pathogenic, proliferative macrophages (as defined by, for example, expression of CD68 and PCNA). These tissues or pathogenic macrophages are then cocultivated with primary macrophages in a suitable culture medium for about one month. The culture can then be examined by electron microscopy of the cells for the presence of viruses. In addition, or alternatively, nucleic acid from the cultured cells can be screened or amplified (e.g., by PCR) using the MHRV-specific primers described herein. The viral nucleic acid can be cloned using methods similar to those described herein for isolation and cloning of MHRV.

Various aspects of the invention based upon the isolated and identification of MHRV are discussed below in more detail.

MHRV Nucleic Acid, Polypeptides, and Polypeptide-Specific Antibodies

The invention features nucleic acid of MHRV, as well as MHRV polypeptides and antibodies that specifically bind such polypeptides. Each of these aspects of the invention is described in more detail below.

MHRV Nucleic Acid

In one aspect, the invention features polynucleotides of MHRV. "MHRV polynucleotides" as used herein generally refers to polynucleotides that can be used to specifically identify MHRV (e.g., as in a nucleic acid probe in detection by hybridization or by sequence analysis) are of particular interest. Exemplary of such polynucleotides are those having at least a portion of a sequence of the GAG gene of MHRV, which sequence is useful in specific detection of MHRV nucleic acid (e.g., in a biological sample). Exemplary MHRV GAG polynucleotide sequences encompassed by the invention include, but are not necessarily limited to, SEQ ID NOS:1 and 7. Exemplary polynucleotides of the invention thus also encompass those having, as a contiguous sequence, a sequence immediately 5' of the MHRV GAG-encoding sequence (e.g., a GAG open reading frame (ORF)) and a sequence within a 5' portion of the MHRV GAG-encoding region are also contemplated by the invention. Likewise, exemplary polynucleotides of the invention include polynucleotides having, as a contiguous sequence, a sequence within a 3' portion of the MHRV GAG-encoding region and a sequence immediately 3' of the MHRV GAG-encoding region.

Other specific, exemplary MHRV polynucleotides contemplated by the invention are those polynucleotides that encode an MHRV GAG polypeptide (about 112 amino acids in length), e.g., the polypeptide of SEQ ID NO:8, as well as polynucleotide that specifically hybridizes to such a polynucleotide molecule or a portion thereof. An MHRV polynucleotide of particular interest is one comprising a sequence encoding a polypeptide having an amino acid sequence of a 5' portion of an MHRV GAG polypeptide, e.g., a polypeptide having at least an N-terminal region of the amino acid sequence of the contiguous amino acid residues 1–22 of SEQ ID NO:8, e.g., at least about 1–4 contiguous amino acid residues from amino acid residues 1–22 of SEQ ID NO:8, at least about 2–5 contiguous amino acid residues from amino acid residues 1–22 of SEQ ID NO:8, at least about 4–10 contiguous amino acid residues from amino acid residues 1–22 of SEQ ID NO:8, at least about 8–15 contiguous amino acid residues from amino acid residues 1–22 of SEQ ID NO:8, at least about 12–20 contiguous amino acid residues from amino acid residues 1–22 of SEQ ID NO:8, up to 22 contiguous amino acid residues from amino acid residues 1–22 of SEQ ID NO:8. Further specific exemplary MHRV polynucleotides include polynucleotides having at least about 10 contiguous nucleotides, at least about 15 contiguous nucleotides, at least about 20 contiguous nucleotides, at least about 50 contiguous nucleotides of SEQ ID NO:7.

The invention also encompasses polynucleotides having sequence complementary to the sequence of the polynucleotides described herein; RNA having a sequence corresponding to DNA sequences described herein; viral genes corresponding to the provided polynucleotides; polynucleotides obtained from the biological materials described herein or other biological sources (particularly human sources) (e.g., by hybridization under stringent conditions, particularly conditions of high stringency); variants of the provided polynucleotides and their corresponding genes, particularly those variants that are present due to the degeneracy of the genetic code (referred to herein as "degenerate variants") and other variants that are specific to MHRV of the invention or retain a biological activity of the gene product encoded by a polynucleotide specifically described herein (e.g., retain the biological activity of the GAG polypeptide in, for example, its reactivity of MHRV GAG-specific antibodies). Other nucleic acid compositions contemplated by and within the scope of the present invention will be readily apparent to one of ordinary skill in the art when provided with the disclosure here.

The polynucleotides of the subject invention can be isolated and obtained in substantial purity, generally as other than an intact chromosome or intact viral particle. Usually, the polynucleotides, either as DNA or RNA, will be obtained substantially free of other naturally-occurring nucleic acid sequences, generally being at least about 50%, usually at least about 90% pure and can be "recombinant", e.g., flanked by one or more nucleotides with which it is not normally associated on a naturally occurring chromosome.

The polynucleotides of the invention can be provided as a linear molecule or within a circular molecule, and can be provided within autonomously replicating molecules (vectors) or within molecules without replication sequences. Expression of the polynucleotides can be regulated by their own or by other regulatory sequences known in the art. The polynucleotides of the invention can be introduced into suitable host cells using a variety of techniques available in the art, such as infection with transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

The host cells suitable for use in production of recombinant host cells can be any prokaryotic or eukaryotic cell suitable for, for example, maintenance and/or replication of vectors containing MHRV nucleic acid, or for replication and production of MHRV viral particles. Exemplary host cells include, but are not necessarily limited to, bacterial, yeast, and mammalian host cells. Isolated recombinant host cells containing MHRV nucleic acid are also contemplated by the invention. Isolated recombinant vectors or constructs containing MHRV nucleic acid are likewise contemplated by the invention. Such vectors can include other components for expression of polypeptides encoded by the MHRV nucleic acid (e.g., promoter elements, transcription termination elements, enhancers, and the like), as well as element for the maintenance, replication, or (optionally) genomic integration of the construct in the host cell (e.g., origin of replication, and the like).

The isolated MHRV polynucleotides of the invention can be provided with 5', 3' or both 5' and 3' flanking sequences. Suitable flanking sequences include, but are not necessarily limited to, promoter sequence, enhancer sequences, transcriptional start and/or stop sites, construct or vector sequences (e.g., sequences that provide for manipulation of the polynucleotide within a linear or circular molecule (e.g., plasmid), including, but not necessarily limited to, sequences for replication and maintenance of the construct or vector, sequences encoding gene products that provide for selection (e.g., antibiotic resistance or sensitivity, factors that affect growth in media with or without supplements, and the like)), sequences that provide for production of a fusion protein with the polynucleotide and a heterologous polypeptide (i.e., a polypeptide encoded by a polynucleotide that originates from a source other than the polynucleotide to which it is operably linked), and the like.

The polynucleotides of the invention include polynucleotides having sequence similarity or sequence identity. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under stringent conditions, for example, at 50° C. or higher and 0.1×SSC (9 mM saline/0.9 mM sodium citrate).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20.×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5×to 1×SSC at 55 to 60° C. Exemplary high stringency conditions include hybridization in 50% formamide, 1 M NaCl, 1% SDS at 37° C., and a wash in 0.1×SSC at 60° to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) Anal. Biochem. 138:267–284: $T_m$=81.5° C.+16.6 (log M)+0.41 (% GC)−0.61 (% form)−500/ L; where M is the molarity of monovalent cations, % GC is the percentage of guanosine and cytosine nucleotides in the DNA, % form is the percentage of formamide in the hybridization solution, and % is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity.

For example, if sequences with up to and including about 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$).

Using the equation, hybridization and wash compositions, and desired $T_m$, those of ordinary skill will understand that variations in the stringency of hybridization and/or wash solutions are within the scope of the present disclosure, as are variations in the lengths of the hybridization and wash steps (e.g., from minutes (e.g., 15 min to 30 min) to hours (e.g., 1–2 hrs to overnight). If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biolog—Hybridization with Nucleic Acid Probes, Part I, Chapter 2 (Elsevier, New York); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, N.Y.).

Nucleic acids of particular interest are those that are substantially identical to the provided polynucleotide sequences (e.g., genetically altered versions of the gene, and the like). Nucleic acids that hybridize to the provided polynucleotide sequences (SEQ ID NOS:1 or 7) under stringent hybridization conditions are also of particular interest. Nucleic acid probes, particularly labeled probes of DNA sequences, can be used to isolate homologous or related MHRV polynucleotides. The source of homologous nucleic acid can be any species, e.g. primate species, particularly human; rodents, such as rats and mice; canines, felines, bovines, ovines, equines, yeast, nematodes, and the like.

Generally, nucleic acid hybridization is performed using at least 15 contiguous nucleotides (nt) of a polynucleotide provided herein. Nucleic acid probes of at least 15 contiguous nt preferentially hybridize with a nucleic acid comprising the complementary sequence, allowing the detection, identification and retrieval of the nucleic acids that uniquely hybridize to the selected probe. Probes of more than 15 nt can be used, e.g., probes of from about 18 nt to about 100 nt in length, but 15 nt represents sufficient sequence for unique identification.

Sequence similarity and sequence identity can also be determined by sequence analysis. In general, sequence identity is calculated based on a reference sequence, which may be a subset of a larger sequence, such as a conserved motif, coding region, flanking region, and the like. A reference sequence will usually be at least about 18 contiguous nt long, more usually at least about 30 nt long, and may extend to the complete sequence that is being compared. Algorithms for sequence analysis are known in the art, such as gapped BLAST, described in Altschul, et al. *Nucleic Acids Res.* (1997) 25:3389–3402. Sequence analysis can be performed using the Smith-Waterman homology search algorithm as implemented in MPSRCH program (Oxford Molecular). For the purposes of this invention, a preferred method of calculating percent identity is determined by the Smith-Waterman homology search algorithm as implemented in MPSRCH program (Oxford Molecular) using an affine gap search with the following search parameters: gap open penalty, 12; and gap extension penalty, 1.

Another embodiment of the invention provides an isolated polynucleotide having at least 85%, at least 88%, at least 90%, at least 92%, at least 94%, at least 96%, at least 98%, or at least 99% sequence identity with the polynucleotides of the invention as described herein. One embodiment provides an isolated polynucleotide having at least 85%, at least 88%, at least 90%, at least 92%, at least 94%, at least 96%, at least 98%, or at least 99% sequence identity with the sequence shown in Table 1. In other embodiments, isolated polynucleotides additionally have less than 85%, 83%, 80%, 75%, 70% sequence identity with the sequence of SEQ ID NO:7.

The nucleic acids of the invention can be cDNAs or isolated as a component of a genomic DNA (e.g., from a patient isolate), as well as fragments thereof, particularly fragments that are useful in the methods disclosed herein (e.g., in diagnosis, as a unique identifier of MHRV nucleic acid, and the like). The term "cDNA" as used herein is intended to include all nucleic acids that share an arrangement of sequence elements that can found in a native mature mRNA species, including splice variants.

The nucleic acid compositions of the invention can encode all or a part of an MHRV polypeptide, e.g., MHRV GAG polypeptide, or can be flanking sequences of the MHRV-polypeptide-encoding region. Double or single stranded fragments can be obtained from the DNA sequence by chemically synthesizing oligonucleotides in accordance with conventional methods, by restriction enzyme digestion, by PCR amplification, and the like. Isolated polynucleotides and polynucleotide fragments of the invention comprise at least about 10, about 15, about 20, about 35, about 50, about 100, about 150 to about 200, about 250 to about 300, or about 350 contiguous nt selected from the polynucleotide sequences as shown in SEQ ID NO:7. In general, fragments will be of at least 15 nt, usually at least 18 nt or 25 nt, and up to at least about 50 contiguous nt in length or more. Nucleic acid fragments of particular interest include a polynucleotide of about 304 contiguous nts and corresponding to a PCR product of an MHRV GAG gene (see, e.g., SEQ ID NO:1).

The subject nucleic acid compositions can be used as single- or double-stranded probes or primers for the detection of MHRV mRNA or cDNA generated from such mRNA, as obtained may be present in a biological sample (e.g., extracts of human cells). The MHRV polynucleotides of the invention can also be used to generate additional copies of the polynucleotides, to generate antisense oligonucleotides, and as triple-strand forming oligonucleotides. These and other uses are described in more detail below.

Nucleic acid probes specific to MHRV can be generated using the polynucleotide sequences disclosed herein. The probes are preferably at least about 12, 15, 16, 18, 20, 22, 24, or 25 nt fragment of a contiguous sequence of SEQ ID NO:7 or other polynucleotide sequence encoding an MHRV GAG polypeptide. Nucleic acid probes can be less than about 200 bp, 150 bp, 100 bp, 75 bp, 50 bp, 60 bp, 40 bp, 30 bp, 25 bp, 2 kb, 1.5 kb, 1 kb, 0.5 kb, 0.25 kb, 0.1 kb, or 0.05 kb in length. The probes can be produced by, for example, chemical synthesis, PCR amplification, generation from longer polynucleotides using restriction enzymes, or other methods well known in the art.

The polynucleotides of the invention, particularly where used as a probe in a diagnostic assay, can be detectably labeled. Exemplary detectable labels include, but are not limited to, radiolabels, fluorochromes,(e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA)), radioactive labels, (e.g. $^{32}$P, $^{35}$S, and $^{3}$H), and the like. The detectable label can involve two stage systems (e.g., biotin-avidin, hapten-anti-hapten antibody, and the like).

The invention also includes solid substrates, such as arrays, comprising any of the polynucleotides described herein. The polynucleotides are immobilized on the arrays using methods known in the art. An array may have one or more different polynucleotides.

MHRV Polypeptides

The polypeptides of the invention include those encoded by the disclosed MHRV polynucleotides, as well as nucleic acids that, by virtue of the degeneracy of the genetic code, are not identical in sequence to the disclosed polynucleotides but encode the same polypeptide. Of particular interest is the MHRV GAG polypeptide, such as that provided in SEQ ID NO:8, as well as variants of such polypeptides, e.g., a polypeptide having the sequence of SEQ ID NO:8, but with conservative amino acid substitutions.

By "MHRV polypeptide" is generally meant a polypeptide that can be obtained from an MHRV viral particle, particularly a polypeptide that can be the basis for specific detection of MHRV virus. Exemplary MHRV polypeptides of particular interest that is specific for MHRV is an MHRV GAG polypeptide (about 112 amino acids in length), e.g., the polypeptide of SEQ ID NO:8 and fragments thereof. An MHRV polypeptide of particular interest is a polypeptide having an amino acid sequence of a 5' portion of an MHRV GAG polypeptide, e.g., a polypeptide having at least an N-terminal region of the amino acid sequence of the contiguous amino acid residues 1-22 of SEQ ID NO:8, e.g., at least about 2-4 contiguous amino acid residues, from amino acid residues 1-22 of SEQ ID NO:8, at least about 2-5 contiguous amino acid residues from amino acid residues 1-22 of SEQ ID NO:8, at least about 4-10 contiguous amino acid residues from amino acid residues 1-22 of SEQ ID NO:8, at least about 8-15 contiguous amino acid residues from amino acid residues 1-22 of SEQ ID NO:8, at least about 12-20 contiguous amino acid residues from amino acid residues 1-22 of SEQ ID NO:8, up to 22 contiguous amino acid residues from amino acid residues 1-22 of SEQ ID NO:8, as well as polypeptides containing such regions.

In general, the MHRV polypeptides of the subject invention are separated from their naturally occurring environment. In certain embodiments, the subject protein is present in a composition that is enriched for the protein as compared to a control. As such, purified polypeptide is provided, where "purified" generally means that the protein is present in a composition that is substantially free of non-differentially expressed polypeptides, where by substantially free is meant that less than 90%, usually less than 60% and more usually less than 50% of the composition is made up of non-differentially expressed polypeptides.

The MHRV polypeptides of the invention include variants of the naturally occurring MHRV protein, where such variants are homologous or substantially similar to the naturally occurring protein, and can be of an origin of the same or different species as the MHRV described herein (e.g., human, murine, or some other species that naturally expresses the recited polypeptide, usually a mammalian species). In general, variant polypeptides have a sequence that has at least about 80%, usually at least about 90%, and more usually at least about 98% sequence identity with a differentially expressed polypeptide of the invention, as measured by BLAST 2.0 using the parameters described above. The variant polypeptides can be naturally or non-naturally glycosylated, i.e., the polypeptide has a glycosylation pattern that differs from the glycosylation pattern found in the corresponding naturally occurring protein. Alternatively, a polypeptide may contain any of the following number of contiguous amino acids of SEQ ID NO:8: 4, 5, 6, 7, 8, 9, 10, 11, 12, 13, 14, 15, 16, 17, 18, 19, 20, 21, and 22 amino acids.

The MHRV polypeptides of the invention also include fragments and fusion proteins having an amino acid sequence of an MHRV polypeptide or a fragment thereof. Of particular interest is an MHRV polypeptide fragment that is specific for MHRV A polypeptide fragment of particular interest is a polypeptide having an amino acid sequence of a 5' portion of an MHRV GAG polypeptide, e.g., a polypeptide having at least an N-terminal region of the amino acid sequence of the contiguous amino acid residues 1-22 of SEQ ID NO:8, e.g., at least about 1-4 contiguous amino acid residues from amino acid residues 1-22 of SEQ ID NO:8, at least about 2-5 contiguous amino acid residues from amino acid residues 1-22 of SEQ ID NO:8, at least about 4-10 contiguous amino acid residues from amino acid residues 1-22 of SEQ ID NO:8, at least about 8-15 contiguous amino acid residues from amino acid residues 1-22 of SEQ ID NO:8, at least about 12-20 contiguous amino acid residues from amino acid residues 1-22 of SEQ ID NO:8, up to 22 contiguous amino acid residues from amino acid residues 1-22 of SEQ ID NO:8.

Also within the scope of the invention are variants; variants of polypeptides include mutants, fragments, and fusions. Mutants can include amino acid substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Conservative amino acid substitutions are those that preserve the general charge, hydrophobicity/hydrophilicity, and/or steric bulk of the amino acid substituted.

MHRV polypeptide fragments are also encompassed by the present invention, particular antigenically effective polypeptide fragments, as well as fragments defining an epitope that can be bound by an antibody that is specific for the MHRV polypeptide. A polypeptide is "antigenically effective" where the polypeptide is effective, either alone or in combination with a carrier protein, to elicit production of antibodies that specifically bind the polypeptide. As used herein, "epitope" refers to an antigenic determinant of a polypeptide. An epitope can comprise about 3 or more amino acids in a spatial conformation which is unique to the epitope. Generally an epitope consists of at least about 5 such amino acids, and more usually, consists of at least about 8-10 such amino acids. Methods of determining the spatial conformation of amino acids are known in the art, and include, for example, x-ray crystallography and 2-dimensional nuclear magnetic resonance.

A polypeptide is "antigenically reactive" with an antibody when it binds to an antibody due to antibody recognition of a specific epitope contained within the polypeptide. Antigenic reactivity may be determined by antibody binding, more particularly by the kinetics of antibody binding, and/or by competition in binding using as competitor(s) a known polypeptide(s) containing an epitope against which the antibody is directed. The techniques for determining whether a polypeptide is antigenically reactive with an antibody are known in the art.

Polypeptide fragments of interest will typically be at least about 10 aa, at least about 15 aa, usually at least about 20 aa to 22 aa, or at least about 50 aa in length, and can be as long as 100 aa in length or longer.

A polypeptide fragment of particular interest is one having at least the N-terminal portion of an MHRV GAG polypeptide, e.g., a polypeptide having at least a portion of a polypeptide defined by amino acid residues 1–22 of an MHRV GAG polypeptide (e.g., amino acid residues 1–22 of SEQ ID NO:8). As discussed in more detail in the Examples below, this N-terminal portion of the MHRV GAG polypeptide is unique to MHRV relative to other retroviruses, and thus can serve as a specific marker for the presence of MHRV in a sample.

Anti-MHRV Antibodies

In yet another embodiment, the invention provides an antibody that specifically binds to an MHRV polypeptide, which polypeptide may be associated with or separate from an MHRV viral particle. The antibody can be generated using isolated, intact MHRV viral particles, an antigenic portion of the virus, an isolated MHRV polypeptide or an antigenic portion of an isolated MHRV polypeptide. Such antibodies are generally referred to herein as anti-MHRV antibodies.

As used herein, the term "antibody" refers to a polypeptide or group of polypeptides which are comprised of at least one antibody combining site. An "antibody combining site" or "binding domain" is formed from the folding of variable domains of an antibody molecule(s) to form three-dimensional binding spaces with an internal surface shape and charge distribution complementary to the features of an epitope of an antigen, which allows an immunological reaction with the antigen. An antibody combining site may be formed from a heavy and/or a light chain domain ($V_H$ and $V_L$, respectively), which form hypervariable loops which contribute to antigen binding. The term "antibody" includes, for example, vertebrate antibodies, hybrid antibodies, chimeric antibodies, altered antibodies, univalent antibodies, the Fab proteins, and single domain antibodies.

Determination of immunogenicity of a protein and generation of an antibody to a virus or a protein are techniques well known in the art (see, for example Harlow and Lane, 1988, supra). By "immunogenic portion" or "immunogenically effective portion" is meant a portion of a virus or viral polypeptide, which is of sufficient size and/or conformation that when injected into an animal causes an immune response and antibodies are generated which bind to the immunogenic portion.

Methods for production of antibodies that specifically bind a selected antigen are well known in the art. Immunogens for raising antibodies can be prepared by mixing an MHRV polypeptide with an adjuvant, and/or by making fusion proteins with larger immunogenic proteins. MHRV polypeptides can also be covalently linked to other larger immunogenic proteins, such as keyhole limpet hemocyanin. Immunogens are typically administered intradermally, subcutaneously, or intramuscularly to experimental animals such as rabbits, sheep, and mice, to generate antibodies. Monoclonal antibodies can be generated by isolating spleen cells and fusing myeloma cells to form hybridomas.

Preparations of polyclonal and monoclonal antibodies specific for polypeptides encoded by a selected polynucleotide are made using standard methods known in the art. Typically, at least 6, 8, 10, or 12 contiguous amino acids are required to form an epitope. Epitopes that involve non-contiguous amino acids may require a longer polypeptide, e.g., at least 15, 25, or 50 amino acids. Antibodies that specifically bind to MHRV polypeptides are generally those that provide a detection signal at least 5-, 10-, or 20-fold higher than a detection signal provided with non-MHRV proteins when used in Western blots or other immunochemical assays. Preferably, antibodies that specifically bind polypeptides of the invention do not bind to other proteins in immunochemical assays at detectable levels and can immunoprecipitate the specific polypeptide from solution.

As noted above, "antibodies" encompasses various kinds of antibodies, including, but not necessarily limited to, naturally occurring antibodies, single domain antibodies, hybrid antibodies, chimeric antibodies, single-chain antibodies, antibody fragments that retain antigen binding specificity, human antibodies, humanized antibodies, and the like. Naturally occurring antibodies specific for MHRV polypeptides, particular for MHRV GAG polypeptides, can be obtained according to methods well known in the art For example, serum antibodies to a polypeptide of the invention in a human population can be purified by methods well known in the art, e.g., by passing antiserum over a column to which MHRV viral particle, or the corresponding selected polypeptide or fusion protein is bound. The bound antibodies can then be eluted from the column, for example using a buffer with a high salt concentration.

The invention also encompasses single domain antibodies, hybrid antibodies, chimeric antibodies, single-chain antibodies, and antibody fragments that retain antigen binding specificity. As used herein, a "single domain antibody" (dAb) is an antibody which is comprised of an VH domain, which reacts immunologically with a designated antigen. A dAb does not contain a $V_L$ domain, but may contain other antigen binding domains known to exist in antibodies, for example, the kappa and lambda domains. Methods for preparing dAbs are known in the art. See, for example, Ward et al. (1989). Antibodies may also be comprised of $V_H$ and $V_L$ domains, as well as other known antigen binding domains. Examples of these types of antibodies and methods for their preparation are known in the art (see, e.g., U.S. Pat. No. 4,816,467, which is incorporated herein by reference), and include the following.

"Vertebrate antibodies" refers to antibodies which are tetramers or aggregates thereof, comprising light and heavy chains which are usually aggregated in a "Y" configuration and which may or may not have covalent linkages between the chains. In vertebrate antibodies, the amino acid sequences of all the chains of a particular antibody are homologous with the chains found in one antibody produced by the lymphocyte which produces that antibody in situ, or in vitro (for example, in hybridomas). Vertebrate antibodies typically include native antibodies, for example, purified polyclonal antibodies and monoclonal antibodies. Examples of the methods for the preparation of these antibodies are described infra.

"Hybrid antibodies" are antibodies wherein one pair of heavy and light chains is homologous to those in a first antibody, while the other pair of heavy and light chains is homologous to those in a different second antibody. Typically, each of these two pairs will bind different epitopes, particularly on different antigens. This results in the property of "divalence", i.e., the ability to bind two antigens simultaneously. Such hybrids may also be formed using chimeric chains, as set forth below.

"Chimeric antibodies", are antibodies in which the heavy and/or light chains are fusion proteins. Typically the constant domain of the chains is from one particular species and/or class, and the variable domains are from a different species and/or class. Also included is any antibody in which either or both of the heavy or light chains are composed of combinations of sequences mimicking the sequences in antibodies of different sources, whether these sources be differing classes, or different species of origin, and whether or not the fusion point is at the variable/constant boundary. Thus, antibodies can be produced in which neither the constant nor the variable region mimic known antibody sequences, thus providing for antibodies having a variable region that has a higher specific affinity for a particular antigen, or having a constant region that can elicit enhanced complement fixation, or to make other improvements in properties possessed by a particular constant region.

The invention also encompasses "altered antibodies", which refers to antibodies in which the naturally occurring amino acid sequence in a vertebrate antibody has been varied. Utilizing recombinant DNA techniques, antibodies can be redesigned to obtain desired characteristics. The possible variations are many, and range from the changing of one or more amino acids to the complete redesign of a region, for example, the constant region. Changes in the constant region, in general, to attain desired cellular process characteristics, e.g., changes in complement fixation, interaction with membranes, and other effector functions. Changes in the variable region may be made to alter antigen binding characteristics. The antibody may also be engineered to aid the specific delivery of a molecule or substance to a specific cell or tissue site. The desired alterations may be made by known techniques in molecular biology, e.g., recombinant techniques, site directed mutagenesis, and other techniques.

Further exemplary antibodies include "univalent antibodies", which are aggregates comprised of a heavy chain/light chain dimer bound to the Fc (i.e., constant) region of a second heavy chain. This type of antibody escapes antigenic modulation. See, e.g., Glennie et al. (1982).

Included also within the definition of antibodies are "Fab" fragments of antibodies. The "Fab" region refers to those portions of the heavy and light chains which are roughly equivalent, or analogous, to the sequences which comprise the branch portion of the heavy and light chains, and which have been shown to exhibit immunological binding to a specified antigen, but which lack the effector Fc portion. "Fab" includes aggregates of one heavy and one light chain (commonly known as Fab'), as well as tetramers containing the 2H and 2L chains (referred to as F(ab).sub.2), which are capable of selectively reacting with a designated antigen or antigen family. "Fab" antibodies may be divided into subsets analogous to those described above, i.e., "vertebrate Fab", "hybrid Fab", "chimeric Fab", and "altered Fab". Methods of producing "Fab" fragments of antibodies are known within the art and include, for example, proteolysis, and synthesis by recombinant techniques.

Assays for Detection of MHRV in a Sample

The invention also contemplates methods of screening biological samples suspected of containing an MHRV sequence. Such screening methods generally involve assays that are based upon detection of MHRV nucleic acid, detection of MHRV polypeptides, or detection of anti-MHRV antibodies.

It will be readily apparent upon reading of the present specification that the assays described herein can be conducted as, or modified to be conducted as, in vitro or in vivo assays, and may be either cell-free (e.g., in vitro binding assays using polynucleotides isolated from or produced from nucleic acid of a biological sample) or cell-based (e.g., screening of whole cells suspected of being infected with MHRV). In general, all assays are conducted under conditions, and for a period of time, sufficient to allow for specific binding of an MHRV-specific probe (e.g., nucleic acid probe, antibody probe, polypeptide probe) to an MHRV probe target, e.g., to provide for detection of MHRV probe target at a detectable level above background. The assays can include various positive and/or negative controls, the nature of which will be readily apparent to the ordinarily skilled artisan upon reading the present specification.

Various aspects of the assays fro detection are described below in more detail

Biological Samples for Detection Assays

Any suitable sample suspected of containing an MHRV viral particle, an MHRV-infected cell, MHRV nucleic acid, MHRV polypeptide, anti-MHRV antibody, and the like. Exemplary samples of interest for screening include, but are not necessarily limited to, biological samples such as blood, blood derivatives, serum, plasma, platelets, mammalian cells (particularly mammalian lymphocytes, more particularly mammalian macrophages, with human cells being of particular interest), tissues (e.g., prior to transplant or other transfer to another subject), and the like. Other exemplary samples of interest for screening include non-biological samples, particularly samples that are on or obtained from a medical instrument, e.g., surgical instruments that, due to their contact with blood and other tissues, could facilitate virus spread if re-used without successfully killing or removing virus.

As will be readily appreciated by the ordinarily skilled artisan, the specific assay selected will vary according to the source of sample and the entity to be detected (e.g., viral particle, nucleic acid, polypeptide, antibody). Examples of various types of assays are provided below. Of particular interest are assays that can be readily conducted in a clinic or in the field, without the need for special tools or detection instruments.

Detection of an MHRV marker in a biological sample indicates that the subject from which the sample was obtained is has been exposed to MHRV, and thus can have an MHRV infection. Detection of MHRV in a subject can also indicate that the subject has, or is at risk of developing, an MHRV-associated disease, such as an MHRV-associated lymphoproliferative disease, e.g., a lymphoma.

Exemplary lymphoproliferative diseases which may be suitable for screening for MHRV, and which may be associated with MHRV include, but are not necessarily limited to: 1) plasma cell disorders (e.g., MGUS, plasmacytoma (including bone and extramedullary plasmacytoma), multiple myeloma, and amyloidosis); 2) Hodgkin's disease; 3) indolent lymphoma/leukemia (including follicle center cell lymphoma and follicular (follicular lymphoma) (e.g., Grade I follicular small cleaved cell; Grade II follicular mixed; and diffuse small cleaved cell lymphoma), diffuse small lymphocytic/chronic lymphocytic leukemia; lymphoplasmacytoid/Waldenstrom's, marginal zone lymphoma (e.g., MALT (extranodal), monocytoid B-cell lymphoma (nodal), and splenic lymphoma with villous lymphocytes), Hairy cell leukemia, and mycosis fungoides/Sezary syndrome; 4) aggressive lymphoma/leukemia (including diffuse large cell lymphoma (includes diffuse mixed cell, diffuse large cell, immunoblastic), Burkitt's lymphoma/diffuse small non-cleaved cell lymphoma, Lymphoblastic lymphoma, CNS lymphoma, Adult T-cell leukemia/lymphoma, Mantle cell lymphoma, Post-transplantation lymphoproliferative disorder, AIDS-related lymphoma (e.g., True histiocytic lymphoma, Primary effusion lymphoma). The classification of the lymphoproliferative is based upon the PDQ modification of the REAL classification as provided by the National Cancer Institute.

Detection of MHRV in a subject can also indicate that the subject has, or is at risk of developing, an MHRV-associated disease, particularly an MHRV-associated chronic disease. Examples of such diseases can include, but are not necessarily limited to terato carcinoma, multiple sclerosis, autoimmune rheumatic diseases, and schizophrenia.

Detection of MHRV in a biological sample also indicates that they biological material form which the biological sample was obtained should not be sued for the purpose of transfer to another subject, as such transfer may result in infection of the recipient.

Exemplary methods for detection of nucleic acid and polypeptide MHRV markers according to the invention are described below.

Methods of Detecting MHRV Nucleic Acid

Any suitable qualitative or quantitative methods known in the art for detecting specific MHRV nucleic acid (e.g., RNA or DNA) can be used. MHRV nucleic acid can be detected by, for example, in situ hybridization in tissue sections, using methods that detect single base pair differences between hybridizing nucleic acid (e.g., using the Invader® technology described in, for example, U.S. Pat. No. 5,846,717), by reverse transcriptase-PCR, or in Northern blots containing poly A+mRNA, and other methods well known in the art. For detection of MHRV polynucleotides in blood or blood-derived samples, the use of methods that allow for detection of single base pair mismatches is preferred.

Using the MHRV nucleic acid as a basis, with MHRV GAG polypeptide-encoding nucleic acid being of particular interest, nucleic acid probes (e.g., including oligomers of at least about 8 nucleotides or more) can be prepared, either by excision from recombinant polynucleotides or synthetically, which probes hybridize with the MHRV nucleic acid, and thus are useful in detection of MHRV virus in a sample, and identification of infected individuals, as well as further characterization of the viral genome(s). The probes for MHRV polynucleotides (natural or derived) are of a length or have a sequence which allows the detection of unique viral sequences by hybridization. While about 6–8 nucleotides may be useful, longer sequences may be preferred, e.g., sequences of about 10–12 nucleotides, or about 20 nucleotides or more. Preferably, these sequences will derive from regions which lack heterogeneity among MHRV viral isolates.

Nucleic acid probes can be prepared using routine methods, including automated oligonucleotide synthetic methods. A complement to any unique portion of the MHRV genome will be satisfactory, e.g., a portion of the MHRV genome that allows for distinguishing MHRV from other viruses that may be present in the sample (e.g., to distinguish the MHRV virus from an endogenous retrovirus such as HERV-K109. For use as probes, complete complementarity is desirable, though it may be unnecessary as the length of the fragment is increased.

For use of such probes as diagnostics, the biological sample to be analyzed, such as blood or serum, may be treated, if desired, to extract the nucleic acids contained therein. The resulting nucleic acid from the sample may be subjected to gel electrophoresis or other size separation techniques; alternatively, the nucleic acid sample may be dot blotted without size separation. The probes are usually labeled with a detectable label. Suitable labels, and methods for labeling probes are known in the art, and include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies.

The probes can be made completely complementary to the MHRV genome or portion thereof (e.g., to all or a portion of a sequence encoding an MHRV GAG polypeptide). Therefore, usually high stringency conditions are desirable in order to prevent or at least minimize false positives. However, conditions of high stringency should only be used if the probes are complementary to regions of the viral genome which lack heterogeneity among MHRV viral isolates. The stringency of hybridization is determined by a number of factors during hybridization and during the washing procedure, including temperature, ionic strength, length of time, and concentration of formamide. These factors are outlined in, for example, Sambrook et al. (1989), "Molecular Cloning; A Laboratory Manual", Second Edition (Cold Spring Harbor Press, Cold Spring Harbor, N.Y.).

Generally, it is expected that the MHRV sequences will be present in a biological sample (e.g., blood, cells, and the liked) obtained from an infected individual at relatively low levels, e.g., at approximately $10^2$-$10^4$ MHRV sequences per $10^6$ cells. This level may require that amplification techniques be used in hybridization assays. Such techniques are known in the art.

For example, the Enzo Biochemical Corporation "Bio-Bridge" system uses terminal deoxynucleotide transferase to add unmodified 3'-poly-dT-tails to a DNA probe. The poly dT-tailed probe is hybridized to the target nucleotide sequence, and then to a biotin-modified poly-A. PCT Publication No. WO84/03520 and European application no. EPA124221 describe a DNA hybridization assay in which: (1) analyte is annealed to a single-stranded DNA probe that is complementary to an enzyme-labeled oligonucleotide; and (2) the resulting tailed duplex is hybridized to an enzyme-labeled oligonucleotide. EPA 204510 describes a DNA hybridization assay in which analyte DNA is contacted with a probe that has a tail, such as a poly-dT tail, an amplifier strand that has a sequence that hybridizes to the tail of the probe, such as a poly-A sequence, and which is capable of binding a plurality of labeled strands.

Non-PCR-based, sequence specific DNA amplification techniques can also be used in the invention to detect MHRV sequences. An example of such techniques include, but are not necessarily limited to the Invader assay, see, e.g., Kwiatkowski et al. *Mol Diagn*. December 1999;4(4):353–64. See also U.S. Pat. No. 5,846,717.

A particularly desirable technique may first involve amplification of the target MHRV sequences in sera approximately 10,000 fold, e.g., to approximately 10 sequences/mL. This may be accomplished, for example, by the polymerase chain reactions (PCR) technique described which is by Saiki et al. (1986), by Mullis, U.S. Pat. No. 4,683,195, and by Mullis et al. U.S. Pat. No. 4,683,202. Other amplification methods are well known in the art.

The probes, or alternatively nucleic acid from the samples, may be provided in solution for such assays, or may be affixed to a support (e.g., solid or semi-solid support). Examples of supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride, diazotized paper, nylon membranes, activated beads, and Protein A beads.

In one embodiment, the probe (or sample nucleic acid) is provided on an array for detection. Arrays can be created by, for example, spotting polynucleotide probes onto a substrate (e.g., glass, nitrocellulose, and the like) in a two-dimensional matrix or array. The probes can be bound to the substrate by either covalent bonds or by non-specific interactions, such as hydrophobic interactions. Samples of polynucleotides can be detectably labeled (e.g., using radioactive or fluorescent labels) and then hybridized to the probes. Double stranded polynucleotides, comprising the labeled sample polynucleotides bound to probe polynucleotides, can be detected once the unbound portion of the sample is washed away. Techniques for constructing arrays and methods of using these arrays are described in EP 799 897; WO 97/29212; WO 97/27317; EP 785 280; WO 97/02357; U.S. Pat. No. 5,593,839; U.S. Pat. No. 5,578,832; EP 728 520; U.S. Pat. No. 5,599,695; EP 721 016; U.S. Pat. No. 5,556,752; WO 95/22058; and U.S. Pat. No. 5,631,734. Arrays are particularly useful where, for example a single sample is to be analyzed for the presence of two or more nucleic acid target regions, as the probes for each of the target regions, as well as controls (both positive and negative) can be provided on a single array. Arrays thus facilitate rapid and convenience analysis.

Methods of Detecting MHRV Polypeptides

In one embodiment, the invention features methods for detecting an MHRV in a sample by detection of an MHRV polypeptide in a sample, which in turn can indicate the presence of MHRV particles in the sample. The sample can be a biological sample, or a sample obtained from, for example, a medical instrument. Biological samples are of particular interest. Of particular interest is detection of an MHRV GAG polypeptide, such as that exemplified by SEQ ID NO:8. Polypeptide-based detection of MHRV can be accomplished by use of a receptor (including ligand-binding receptor fragments) or an antibody (including antigen-binding antibody fragments) that specifically binds the target MHRV polypeptide (e.g., an anti-MHRV GAG polypeptide antibody).

Polypeptide-based detection of MHRV can be accomplished using a variety of biological samples, e.g., blood or blood derivatives (e.g., serum, plasma, and the like), cells, tissues, and the like. The anti-MHRV antibody can be generated so as to detect the MHRV polypeptide on a surface of an infected host cell, on the surface of an MHRV viral particle, or as free polypeptide (e.g., not associated with either a host cell or a viral particle, such as may be present in a sample due to lysis of the viral particle or infected host cell).

In one embodiment, the invention features immunoassays to determine the presence of MHRV polypeptide (including MHRV polypeptide present on viral particles) in a biological sample, e.g., a cell or a body fluid sample, by contacting the sample with an antibody (usually, but not necessarily, a monoclonal antibody); reacting the sample and the antibody for a time and under conditions that allow the formation of an immunocomplex between the antibody and MHRV virus particles and/or MHRV polypeptide in the sample; and detecting the immunocomplex. The presence of an immunocomplex indicates the presence of MHRV polypeptide in the sample.

Design of the immunoassays is subject to a great deal of variation, and many formats are known in the art. The immunoassay will utilize at least one viral epitope derived from MHRV. In one embodiment, the immunoassay uses a combination of viral epitopes derived from MHRV. These epitopes may be derived from the same or from different viral polypeptides, and may be in separate recombinant or natural polypeptides, or together in the same recombinant polypeptides. An immunoassay may use, for example, a monoclonal antibody directed towards a viral epitope(s), a combination of monoclonal antibodies directed towards epitopes of one viral antigen, monoclonal antibodies directed towards epitopes of different viral antigens, polyclonal antibodies directed towards the same viral antigen, or polyclonal antibodies directed towards different viral antigens.

Protocols may be based, for example, upon competition, or direct reaction, or sandwich type assays. Protocols may also, for example, use solid supports, or may be by immunoprecipitation. Most assays involve the use of labeled antibody or polypeptide; the labels may be, for example, enzymatic, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

The immunoassay may be, without limitations, in a heterogeneous or in a homogeneous format, and of a standard or competitive type. In a heterogeneous format, the anti-MHRV antibody is typically bound to a solid support to facilitate separation of the sample from MHRV polypeptide after incubation. The solid support containing the is typically washed after reaction for a time sufficient to allow for antibody-antigen complex formations (e.g., about 10 min) prior to detection of bound antibodies. Both standard and competitive formats are known in the art.

In a homogeneous format, the test sample is incubated with anti-MHRV antibody in solution. For example, it may be under conditions that will precipitate any antigen-antibody complexes which are formed. Both standard and competitive formats for these assays are known in the art.

In a standard format, the level of MHRV polypeptide-antibody complex is directly monitored. This may be accomplished by, for example, determining whether labeled anti-xenogenic (e.g., anti-human) antibodies which recognize an epitope on anti-MHRV antibodies will bind due to complex formation. In a competitive format, the amount of MHRV polypeptide in the sample is deduced by monitoring the competitive effect on the binding of a known amount of labeled MHRV polypeptide (or other competing ligand) in the complex. Amounts of binding or complex formation can be determined either qualitatively or quantitatively.

Complexes formed comprising MHRV polypeptide and anti-MHRV antibody are detected by any of a number of known techniques, depending on the format. For example, unlabeled MHRV antibodies in the complex may be detected using a conjugate of antixenogeneic Ig complexed with a label, (e.g., an enzyme label).

The antibody in the immunoassays for detection of MHRV polypeptides may be provided on a support (e.g., solid or semi-solid); alternatively, the polypeptides in the sample can be immobilized on a support. Examples of supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride, diazotized paper, nylon membranes, activated beads, and Protein A beads. Bead-based supports are generally more useful for immobilization of the antibody in the assay.

In one embodiment, the biological sample contains cells (e.g., whole cells) and detection is by reacting the sample with labeled antibodies, performed in accordance with conventional methods. In general, antibodies that specifically bind an MHRV polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, and others). The absence or presence of antibody binding can be determined by various methods, including, but not limited to, flow cytometry of dissociated cells, microscopy, radiography, and scintillation counting. Any suitable alternative methods of qualitative or quantitative detection of levels or amounts of differentially expressed polypeptide can be used, for example ELISA, western blot, immunoprecipitation, radioimmunoassay, and the like.

In another embodiment of this assay, the immunocomplex can be detected by a competitive immunoassay by reacting the anti-MHRV antibody with the sample and with a competing antigen to which the antibody is known to specifically bind, e.g., a detectably labeled MHRV antigen or an immobilized competing antigen such as an isolated viral protein. The competing antigen can be labeled or immobilized.

Alternatively, the immunoassay is a sandwich immunoassay that uses a second antibody, e.g., a monoclonal antibody, that either also binds MHRV viral particles or binds to the first monoclonal antibody, one of the two antibodies being immobilized and the other being labeled using standard techniques. In the sandwich immunoassay procedures, the MHRV viral particle-binding antibody can be a capture antibody attached to an insoluble material, and the second MHRV viral particle-binding antibody can be a detector or labeling antibody.

Methods of Detecting Anti-MHRV Antibodies

In another aspect, the presence of MHRV in a host may be detectable by assaying an appropriate biological sample from the host for anti-MHRV antibodies. Of particular interest if the detection of anti-MHRV GAG polypeptide antibodies. Various methods for detection of an anti-MHRV antibody in a biological sample are well known in the art.

Anti-MHRV antibodies are can be detected by, for example, obtaining a biological sample from a patient having or suspected of having an MHRV infection (e.g., suspected of having an MHRV-associated lymphoma), and which biological sample is suspected of containing an antibody that specifically binds to MHRV. The biological sample of the patient is contacted with an isolated MHRV particle or with an MHRV GAG polypeptide or antigenic fragment thereof. Formation of antibody-viral particle or antibody-polypeptide complexes is monitored by standard techniques (see, for example, Harlow and Lane, 1988, Antibodies: A Laboratory Manual, Cold Spring Harbor Laboratory Press, Cold Spring Harbor, N.Y.).

Typically, an immunoassay for an anti-MHRV antibody(s) will involve selecting and preparing the test sample suspected of containing the antibodies, such as a biological sample, then incubating it with an antigenic (e.g., epitope-containing) MHRV polypeptide(s) under conditions that allow antigen-antibody complexes to form, and then detecting the formation of such complexes. Suitable incubation conditions are well known in the art.

Antibodies in the test sample that cross react with non-MHRV particles or non-MHRV polypeptides can be depleted from the test sample using standard control screening steps where desired. Variations on methods of detecting anti-MHRV antibodies are similar to those described above for detection of MHRV viral particles and/or MHRV polypeptides and other variations that will be readily apparent to the ordinarily skilled artisan upon reading the present specification.

The immunoassays for detection of anti-MHRV polypeptide antibodies may be conducted using an MHRV polypeptide on a support (e.g., solid or semi-solid); alternatively, the antibodies in the sample can be immobilized on a support fro contacting with an MHRV polypeptide. Examples of supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride, diazotized paper, nylon membranes, activated beads, and Protein A beads. Bead-based supports are generally more useful for immobilization of the MHRV polypeptide in this embodiment of the invention.

In an exemplary embodiment, screening for anti-MHRV antibodies in a sample is accomplished by contacting a biological sample with an isolated MHRV polypeptide. An interaction between an antibody in the sample and the MHRV protein is monitored by standard techniques (see, for example, Harlow and Lane, 1988, supra). Detection of antibody-MHRV polypeptide complexes indicates that the ample contains anti-MHRV antibodies, and in turn that the patient has generated a humoral response against MHRV, which in turn indicates that the patient is infected with or at least has been exposed to MHRV.

Pharmaceutical Compositions

The invention further contemplates pharmaceutical compositions comprising at least one of an MHRV polypeptide or an MHRV polynucleotide, which is provided in a pharmaceutically acceptable excipient. Various pharmaceutically acceptable excipients are well known in the art. As used herein, "pharmaceutically acceptable excipient" includes any material which, when combined with an active ingredient of a composition, allows the ingredient to retain biological activity and without causing disruptive reactions with the subject's immune system.

Exemplary pharmaceutically carriers include sterile aqueous of non-aqueous solutions, suspensions, and emulsions. Examples include, but are not limited to, any of the standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition of an MHRV polypeptide or MHVE polynucleotide may also be lyophilized using means well known in the art, for subsequent reconstitution and use according to the invention. Also of interest are formulations for liposomal delivery, and formulations comprising microencapsulated MHRV polypeptides or MHRV polynucleotides. Compositions comprising such excipients are formulated by well known conventional methods (see, for example, Remington's Pharmaceutical Sciences, Chapter 43, 14th Ed., Mack Publishing Col, Easton, Pa. 18042, USA).

In general, the pharmaceutical compositions can be prepared in various forms, such as granules, tablets, pills, suppositories, capsules (e.g. adapted for oral delivery), microbeads, microspheres, liposomes, suspensions, salves, lotions and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Stabilizing agents, wetting and emulsifying agents, salts for varying the osmotic pressure or buffers for securing an adequate pH value.

Kits

Reagents specific for MHRV polynucleotides, MHRV viral particles, MHRV polypeptides, and/or anti-MHRV antibodies can be supplied in a kit for detecting the presence or absence of an MHRV polynucleotide, or an expression product of an MHRV, in a biological sample. Such reagents can include, for example, nucleotide probes or primers for detection of MHRV nucleic acid, anti-MHRV antibodies for detection of MHRV viral particles and/or polypeptides, and MHRV polypeptides for detection of anti-MHRV antibodies in the sample. The reagents can be provided in labeled vials. The kit can also include buffers or labeling components, as well as instructions for using the reagents to detect (either qualitatively or quantitatively) the target nucleic acid, polypeptide, or antibody in the biological sample. The kit can further include appropriate positive controls, negative controls, or both.

For example, nucleic acid probes can be packaged into diagnostic kits. Diagnostic kits can include one or more polynucleotide probes (e.g., DNA or RNA) which may be labeled; alternatively, the polynucleotide probe may be unlabeled and the ingredients for labeling may be included in the kit in separate containers. The kit may also contain other suitably packaged reagents and materials needed for the particular hybridization protocol, for example, standards, as well as instructions for conducting the test.

Kits suitable for immunodiagnosis and containing the appropriate labeled reagents are constructed by packaging the appropriate materials, including the polypeptides of the invention containing MHRV epitope(s) or antibodies directed against MHRV epitope(s) in suitable containers, along with the remaining reagents and materials required for the conduct of the assay, as well as a suitable set of assay instructions. Assays using the kits may be performed in vitro and cell-free (e.g., in vitro binding assays) or may be cell-based.

Cell Culture Systems and Animal Model Systems for MHRV Replication

The finding that MHRV has similarities to a human endogenous retrovirus provides information on methods for propagating MHRV. MHRV is thought to be similar to HERVs based on sequence analysis, as described in more detail below. Generally, suitable cells or cell lines for culturing MHRV may include those known to support retroviral replication, with cells and cell lines of the same lineage as macrophages being of particular interest. Useful cells or cell lines for MHRV propagation can include human cells and cell lines, and non-human cells and cell lines (e.g., porcine, rat, and the like) Exemplary cells useful in this regard include, but are not necessarily limited to, macrophage derived cell populations such as dendritic cells, Langerhans cells, microglial cells, as well as cell lines derived from any of these primary cell populations. Macrophage like tumor cell lines (e.g., THP-1 cells) may also be useful in culturing MHRV.

MHRV may also be propagated in primary cultures of macrophages, which cultures can be infected with MHRV. Alternatively, the macrophage cultures can be derived from the infected individuals. The latter case is an example of a cell which is infected in vivo being passaged in vitro. In addition, various immortalization methods can be used to obtain cell-lines derived from macrophage cultures. For example, primary macrophage cultures (before and after enrichment of the desired population) may be fused to a variety of cells to maintain stability. Alternatively, cultures may be infected with transforming viruses, or transfected with transforming genes in order to create permanent or semipermanent cell lines. It is noted that since MHRV is associated with development of lymphoma, MHRV may alone effect transformation of the cells to produce stable cell lines in culture.

As discussed above, MHRV is a retrovirus. Therefore, it is probable that MHRV infection of cell lines may be accomplished by techniques known in the art for infecting cells with other retroviruses. These include, for example, incubating the cells with viral preparations under conditions which allow viral entry into the cell. In addition, it may be possible to obtain viral production by transfecting the cells with isolated viral polynucleotides. Methods for transfecting tissue culture cells with viral genomic nucleic acid, or cDNA derived from such viral genomic nucleic acid, are known in the art, and include, for example, techniques which use electroporation, and precipitation with DEAE-Dextran or calcium phosphate. An abundant source of MHRV RNA can be obtained by performing in vitro transcription of an MHRV cDNA corresponding to the complete genome. Transfection with this material, or with cloned MHRV cDNA should result in viral replication and the in vitro propagation of the virus.

In addition to cultured cells, animal model systems may be used for viral replication; animal systems in which retroviruses are known to those of skill in the art. On exemplary animal model is the scid mouse. Further exemplary models include, but are not necessarily limited to, primates (e.g., monkeys, chimpanzees, orangutans, and the like).

Identification of Anti-MHRV Agents

The invention is also directed to methods for identifying anti-viral agents for MHRV. Exemplary MHRV anti-viral agents include those that inactivate the virus (e.g., by treatment of an instrument or biological material (e.g., blood) prior to use), inhibit MHRV entry into a host cell, inhibit MHRV replication, or otherwise disrupt or interfere with MHRV pathogenesis. Those agents that allow growth and proliferation of the infected cell while inhibiting viral replication are of particular interest, with agents that facilitate inhibition of growth of infected cells, up to and including death of such cells, also being of interest. Since MHRV is associated with lymphoma, agents that act as anti-cancer agents by virtue of their affect upon MHRV are also of interest.

The term "agent" as used herein describes any molecule, e.g., protein or pharmaceutical, which is amenable for screening for anti-MHRV activity (e.g., activity in inhibiting replication, infection, or other aspect of MHRV infection and propagation). Generally, pluralities of assay mixtures are run in parallel with different agent concentrations to detect differential responses to the various concentrations. Typically, one of these concentrations serves as a negative control, i.e., at zero concentration or below the level of detection.

Candidate agents encompass numerous chemical classes, though typically they are organic molecules, and are generally small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, pheromones, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs.

Various screening methods useful in the present invention are known by those of skill in the art. Generally, the anti-viral agents are tested at a variety of concentrations, for their effect on preventing viral replication in cell culture systems which support viral replication, and then for an inhibition of infectivity or of viral pathogenicity (and a low level of toxicity) in an animal model system. Exemplary methods include, but are not necessarily limited to, assays to determine the effect of the agent upon viral $ID_{50}$ or upon the ability of the virus to induce cell plaque formation.

The methods and compositions provided herein for detecting MHRV polypeptides and MHRV polynucleotides are useful for screening of anti-viral agents in that they provide an alternative, and sensitive, means for detecting the agent's effect on viral replication than the cell plaque assay or $ID_{50}$ assay.

For example, the MHRV-polynucleotide probes described herein may be used to quantitate the amount of viral nucleic acid produced in a cell culture. This could be accomplished, for example, by hybridization or competition hybridization of the infected cell nucleic acids with a labeled MHRV-polynucleotide probe. For example, also, anti-MHRV antibodies may be used to identify and quantitate MHRV antigen(s) in the cell culture utilizing the immunoassays described herein. In addition, since it may be desirable to quantitate MHRV antigens in the infected cell culture by a competition assay, the polypeptides encoded within the MHRV cDNAs described herein are useful in these competition assays. Generally, a recombinant MHRV polypeptide derived from the MHRV cDNA would be labeled, and the inhibition of binding of this labeled polypeptide to an MHRV polypeptide due to the antigen produced in the cell culture system would be monitored. Moreover, these techniques are particularly useful in cases where the MHRV may be able to replicate in a cell line without causing cell death.

The anti-viral agents which may be tested for efficacy by these methods are known in the art, and include, for example, those which interact with virion components and/or cellular components which are necessary for the binding and/or replication of the virus. Typical anti-viral agents may include, for example, inhibitors of virion polymerase and/or protease(s) necessary for cleavage of the precursor polypeptides. Other anti-viral agents may include those which act with nucleic acids to prevent viral replication, for example, anti-sense polynucleotides, etc.

Antisense polynucleotides molecules, which are comprised of a complementary nucleotide sequence which allows them to hybridize specifically to designated regions of genomes or RNAs, is an example of an anti-MHRV viral agent of interest that can be identified through screening assays according to the invention. Antisense polynucleotides may include, for example, molecules that will block protein translation by binding to mRNA, or may be molecules which prevent replication of viral RNA by transcriptase. They may also include molecules which carry agents (non-covalently attached or covalently bound) which cause the viral RNA to be inactive by causing, for example, scissions in the viral RNA. They may also bind to cellular polynucleotides which enhance and/or are required for viral infectivity, replicative ability, or chronicity. Antisense molecules which are to hybridize to MHRV derived RNAs may be designed based upon the sequence information of the MHRV cDNAs provided herein. The antiviral agents based upon anti-sense polynucleotides for MHRV may be designed to bind with high specificity, to be of increased solubility, to be stable, and to have low toxicity. Hence, they may be delivered in specialized systems, for example, liposomes, or by gene therapy. In addition, they may include analogs, attached proteins, substituted or altered bonding between bases, and the like.

Other types of drugs having anti-MHRV activity may be based upon polynucleotides which "mimic" important control regions of the MHRV genome, and which may be therapeutic due to their interactions with key components of the system responsible for viral infectivity or replication.

Use of MHRV Agents

The anti-MHRV agents identified as described herein, or other anti-MHRV agents, can be used to treat MHRV infections in a subject, where "subject" encompasses all host susceptible to MHRV infection, with mammals, particularly humans, being of particular interest. Since, MHRV carries a reverse transcriptase and protease enzyme, both of which have been successful targets for anti-HIV therapeutics, agents that act in a similar manner may find particular use in treatment of MHRV infection. In addition, blood macrophages isolated from patients with MHRV associated mantle cell lymphoma are abnormal (express PCNA, consistent with proliferation) and are killed by polyamine analogues in vitro.

"Polyamines" generally refer to any of a group of aliphatic, straight-chain amines derived biosynthetically from amino acids; polyamines are reviewed in Marton et al. (1995) *Ann. Rev. Pharm. Toxicol.* 35:55–91. Polyamines can be, for example, a naturally-occurring polyamine or natural polyamine, which are naturally produced in eukaryotic cells. Examples of polyamines include putrescine, spermidine, spermine and cadaverine. "Polyamine analogs" generally refer to an organic cation structurally similar but non-identical to naturally-occurring polyamines such as spermine and/or spermidine and their precursor, diamine putrescine. Polyamine analogs can be branched or un-branched, or incorporate cyclic moieties. Examples of polyamine analogs include, without limitation, $N^1$, $N^{14}$-diethylhomo-spermine (DEHSPM) and $N^1$, $N^{12}$-diethylspermine (DESPM). See, for example, WO 98/17624 and U.S. Pat. No. 5,541,230. U.S. Pat. Nos. 5,037,846 and 5,242,947 disclose polyamines comprising primary amino groups. Especially preferred are polyamine analogs wherein all nitrogen atoms of said polyamine analogs are independently secondary, tertiary, or quaternary amino groups.

For a discussion of polyamine analogs that may be suitable for use in treatment of MHRV, as well as formulations, compositions, and methods of delivery, see, e.g., PCT publication no. WO 99/21542. Any suitable polyamine analog, or stereoisomers, salts or protected derivatives thereof (or a composition comprising an effective amount of a polyamine analog, or stereoisomers, salts or protected derivatives thereof) may be administered, generally according to the manufacturer's/supplier's instructions. Generally, polyamine analogs are administered by subcutaneous or intravenous injection. They may also be administered orally.

The amount of a polyamine analog (or stereoisomers, salts or protected derivatives thereof) administered will depend on several variables, such as the particular analog (or stereoisomer, salt or protective derivative) used, the time course of administration, the condition of the individual, the desired objective, the extent of disease, how many doses will be administered, and whether any other substances are being administered. Generally, the amount used will be as recommended by the manufacturer and/or based on empirical studies. In the case of polyamine analogs (or stereoisomer, salt, or protected derivative thereof), the amount will generally be between about 1 to about 300 mg/m$^2$/day, possibly between about 15 to about 150 mg/m$^2$/day. Administration is generally intermittent, meaning that analog (or stereoisomer, salt, or protected derivative thereof) is administered per a period of at least one to two days and then not administered for a period of at least one to two days, with the cycle repeated as indicated. In one embodiment, the polyamine analog (or stereoisomer, salt, or derivative thereof) for 6 days every three weeks.

Routes of administration will generally depend on the nature of the particular polyamine analog (or stereoisomer, salt or protective derivative) used, and may be, for example, oral or by injection (subcutaneous or intravenous). Administration is generally by intravenous or subcutaneous injection.

Generally, a polyamine analog (or stereoisomer, salt or protected derivative), or other suitable agent that interferes with the polyamine synthetic pathway, polyamine metabolism, and/or the intracellular concentration maintenance of spermine) is administered in a composition comprising a suitable pharmaceutical excipient. Pharmaceutical excipients are known in the art and are set forth in *Remington's' Pharmaceutical Sciences,* 18th edition, Mack Publishing (1990). The polyamine analog may also be associated with another substance that facilitates agent delivery to macrophages, or increases specificity of the agent to macrophages. For example, an agent(s) may be associated into liposomes. Liposomes are known in the art. The liposomes in turn may be conjugated with targeting substance(s), such as IgGFc receptors. Substances that increase macrophage phagocytosis such as zymosan or tetrachlorodecaoxygen (TCDO) and/or activation such as MCSF, GMCSF or IL-3 may be used to increase uptake of anti-proliferative agent(s).

Other agents can be administered in conjunction with (either prior to, with, or after) administration of an anti-MHRV agent.

Preparation of Attenuated Strains of MHRV

In addition to the above, utilizing the tissue culture systems and/or animal model systems, attenuated strains of MHRV can be constructed and/or isolated. These strains would be suitable for vaccines, or for the isolation of viral antigens.

Attenuated strains are isolatable after multiple passages in cell culture and/or an animal model. Detection of an attenuated strain in an infected cell or individual can be accomplished by techniques known in the art, and could include, for example, the use of antibodies to one or more epitopes encoded in MHRV as a probe or the use of a polynucleotide containing an MHRV sequence of at least about 8 nucleotides as a probe.

Alternatively, or in addition, an attenuated strain may be constructed utilizing the genomic information of MHRV provided herein, and utilizing recombinant techniques. Generally, deletion mutants of MHRV would be generated by deleting a region of the genome encoding, for example, a polypeptide related to pathogenicity, but which allows for at least some level of viral replication so as to effect an effective immune response to MHRV antigens to the vaccinated host. In addition, the genome construction would allow the expression of an epitope which gives rise to neutralizing antibodies for MHRV. The altered genome could then be utilized to transform cells which allow MHRV replication, and the cells grown under conditions to allow viral replication.

In addition to their uses as vaccines, attenuated MHRV strains can also be used as sources for the commercial production of viral antigens. An attenuated virus for vaccine purposes can, for example, contain antigenic sites defined by study of diseased versus non-diseased-MHRV infected individuals in a form that infects primary macrophages. Such antigenic structures can then be expressed and isolated for use in vaccines.

MHRV-Based Viral Vectors

The MHRV genome can be used as the basis of a viral vector, e.g., a shuttle vector, which can be used to generate recombinant MHRV vectors for manipulation and transfer of a recombinant nucleic acid encoding a gene product of interest. In one embodiment, the MHRV vectors of the invention comprise all or a portion of an MHRV genome which is modified to comprise a cloning site, preferably a multiple cloning site, which provides for a restriction site, preferably a unique restriction site, so as to facilitate insertion and ligation of a nucleic acid of interest. "Restriction site" as used herein is meant to refer to a nucleic acid sequence that is recognized and cleaved by a restriction enzyme. In another embodiment, a nucleic acid encoding a gene product of interest, which nucleic acid is heterologous to the MHRV genome (i.e., is a nucleic acid not normally found in an MHRV genome), is inserted in a naturally-occurring, preferably unique, restriction site in the MHRV genome. Preferably, the nucleic acid of interest is operably inserted in the vector so as to provide for expression of the encoded gene product in a host cell (in vitro or in vivo) upon introduction of the MHRV vector into the host cell.

In one embodiment, expression of the recombinant MHRV vector in a suitable host cell provides for a replication competent recombinant MHRV viral particle, which is modified to contain a sequence encoding a gene product of interest. The cloning site and/or the recombinant, introduced nucleic acid of interest, can be inserted into the MHRV genome at any suitable site. In a specific embodiment, the cloning site and/or recombinant nucleic acid is inserted adjacent the MHRV genome pol region.

Figure 4:
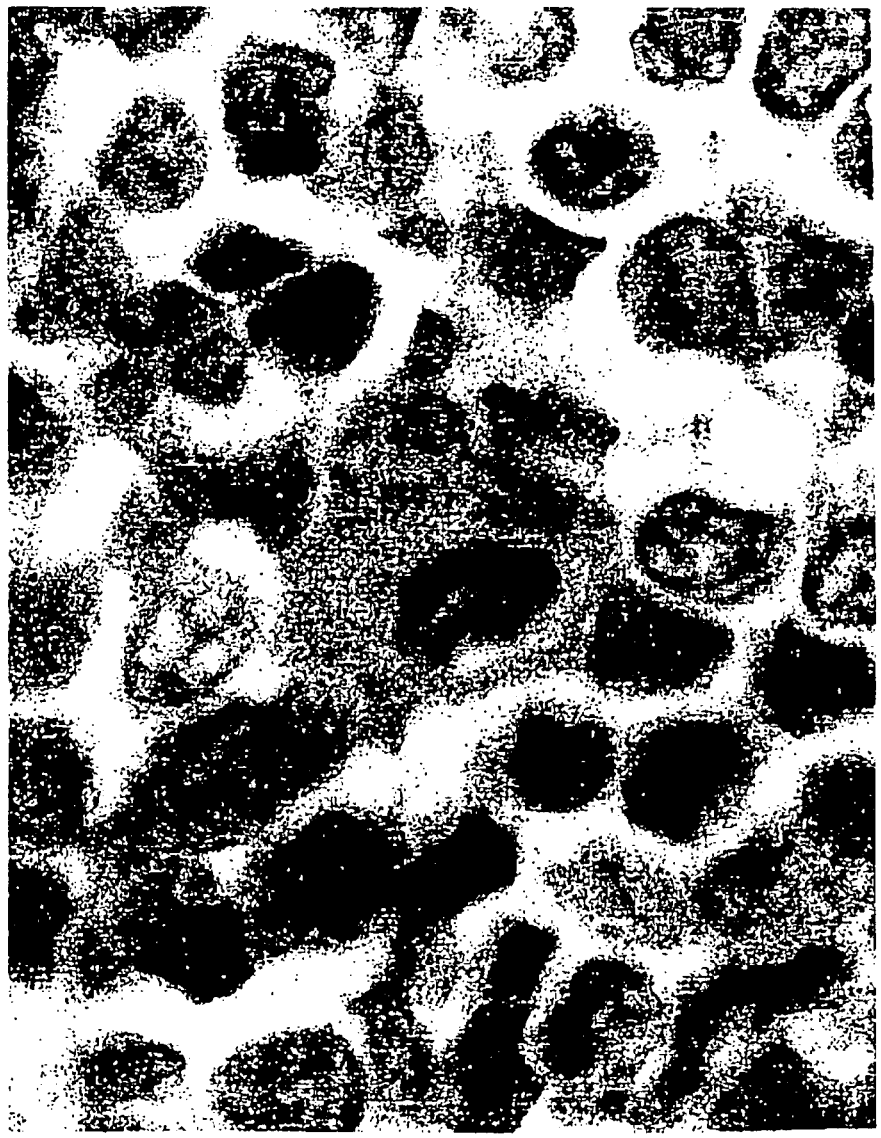
FIG. 4 is a photograph showing the histology of the mantle cell lymphoma from which MHRV was isolated.

In another embodiment, the MHRV vector is rendered replication defective, e.g. by deletion or other modification to render the Gag envelope protein-encoding sequence, the polymerase (pol)-encoding sequence, or both nonfunctional. IN a specific embodiment, the cloning site and/or recombinant nucleic acid is inserted in the MHRV genome pol region so as to disrupt the polymerase-encoding sequence. The replication defective vector is then modified to include a sequence encoding a gene product. Recombinant MHRV particles are then produced in vitro by introducing the recombinant, replication-defective MHRV vector into a packaging cell (generally a mammalian cell) that is modified to express (either constitutively or inducibly) the necessary viral components required for production of the MHRV viral particle, e.g., a cell that expresses the MHRV gag, MHRV pol, or both as necessary to complement the modified elements of the recombinant MHRV vector. Co-expression of the MHRV vector in this modified recombinant host cell results in production of viral particles, which can then be isolated (e.g., from the supernatant) and used to infect target cells.

The recombinant nucleic acid for insertion in the recombinant MHRV vector can be any nucleic acid of interest encoding any gene product of interest. The MHRV vector or MHRV viral particles can be used to modify a host cell either in vitro (e.g., for ex vivo therapy) or in vivo. For example, the recombinant MHRV viral particles of the invention can be used to deliver a secreted polypeptide for production in a host cell in vivo for purposes of long term secretion of any soluble protein in which the patient is deficient or from which the patient would derive a therapeutic benefit. For example, recombinant MHRV particles can be used to deliver a gene encoding a blood clotting (e.g., factor VIII) into macrophages prepared from autologous blood, which modified macrophages can be infused back into the host to provide a source of factor VIII, thereby alleviating hemophilia.

Recombinant MHRV vectors and recombinant MHRV viral particles are particularly attractive as gene delivery vehicles, in that MHRV efficiently infect non-dividing cells, e.g., non-dividing macrophages, a characteristic not shared by the majority of retroviruses currently used in gene therapy. Thus recombinant MHRV vectors and recombinant MHRV viral particles may find particular use in delivery of gene products to or via such non-dividing cells, e.g., macrophages, stem cells, and the like.

Deposits

A deposit of biologically pure cultures of the MHRV strain MRV-med- 6/01 is available upon request from the laboratory of Michael S. McGarth at the University of California, San Francisco, Box 0874, San Francisco, CA 94043, U.S.A., and was made on or before the filing date of the present application. The strain of the deposit indicated underwent successful viability testing. Access to said cultures will be available during pendency of the patent application to one determined by the Commissioner to be entitled to such under 37 C.F.R. §1.14 and 35 U.S.C. §122. All restriction on availability of said cultures to the public will be irrevocably removed upon the granting of a patent based upon the application. Moreover, the designated strain of the deposit will be maintained for a period of thirty (30) years from the date of deposit, or for five (5) years after the last request for the deposit; or for the enforceable life of the U.S. patent, whichever is longer. Should a culture become non-viable or be inadvertently destroyed, it will be replaced with a viable culture(s) of the same taxonomic description.

Access to the MRV-med-6/01 strain of the deposit is provided merely as a convenience to those of skill in the art, and is not an admission that such access is required. A license may be required to make, use, or sell the deposit or related materials, and no such license is hereby granted.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, molecular weights) but some experimental errors and deviations should be accounted for. Unless indicated otherwise, parts are parts by weight, molecular weight is weight average molecular weight, temperature is in degrees Centigrade, and pressure is at or near atmospheric.

Example 1

Patients with Lymphoma have Circulating Activated Macrophages

Activated macrophages have been previously identified in the blood of patients with AIDS dementia (Pulliam et al. *Lancet* 349:692–695 (1997)). In preliminary studies, it was noted that patients with lymphoma also had unusual circulating macrophages that appeared "activated" by virtue of high side scatter (flow cytometric light scattering of CD14 expressing cells) and activation markers such as CD69. Studies of these macrophages showed that they were both activated and proliferating, staining with the proliferation markers PCNA, Ki-67. These cells also took up bromodeoxyuridine, a characteristic of proliferating cells.

A summary of percent PCNA staining on peripheral blood CD14 cells derived from patients with AIDS lymphoma and non-AIDS lymphoma as compared to blood from laboratory workers is shown in FIG. 2. PCNA staining was accomplished by obtained whole blood form AIDS and non-AIDS lymphoma patients, and laboratory worker controls. Peripheral blood mononuclear cells were isolated from the samples, and the cells fixed, permeabilized, and stained with anti-PCNA antibodies according to methods well known in the art. Staining for CD14 on the cells served as a control. Percent PCNA above background of CD14 cells was calculated and plotted. Values obtained for controls (n=13), HIV-non-Hodgkin's lymphoma (NHL) (n=16), non-HIV-NHL (n=18) were each calculated. A 30% PCNA+value served as a cutoff for conferring a positive value. As shown in FIG. 2, both AIDS and non-AIDS lymphoma patients had a higher frequency of elevated PCNA+CD14 cells (>30%, p=0.03, 0.006 respectively) in their blood than did control (age 25–45) laboratory workers. Studies of patients with the highest levels of PCNA+CD14 cells revealed them to have chronic lymphomas of an indolent nature (follicular lymphoma, mantle cell lymphoma, mycosis fungoides). These PCNA+macrophages were also observed in AIDS lymphoma tissue specimens.

Studies were performed on a non-AIDS follicular lymphoma specimen to determine whether macrophages or macrophage like cells showed evidence for proliferation.

FIG. 3 shows a histological section containing a follicular dendritic cell in a low grade follicular lymphoma undergoing mitosis, suggesting the capability of this cell population for pathogenic proliferation. Furthermore, the mitotic figure is tripolar an abnormality thought to be diagnostic of malignancy. These data suggest that potentially pathogenic macrophage like cells can be identified in non-AIDS lymphoma.

Example 2

Characterization of a Novel Human Retrovirus, MHRV

An index case of non-Hodgkin's lymphoma containing macrophages with characteristics consistent with those described in AIDS lymphoma was utilized in a virus isolation attempt. The histology of this mantle cell lymphoma is shown in FIG. 4. The protocol for virus isolation and cultivation was as follows:

MHRV Cultivation in Human Macrophages

The mantle histiocyte retrovirus (MHRV) was cultivated in human macrophages, and recovered from the cultured cells and medium for analysis. The protocols used are described below.

1) Original material: The original mantle cell lymphoma material was identified by Dr. Herndier who identified MCL-1 (patient LL) as a likely candidate tissue based on ultrastructural similarities observed in this tissue as compared to HIV lymphoma associated macrophages. The patient was a 51 year old man who was negative for HIV, HBV and HCV.

2) Macrophage preparations: Blood was obtained from the Stanford Blood center. Blood was drawn, prepared, and stored overnight at room temperature. Macrophages were then obtained from the blood the following morning as follows. The bags were cut open and an equal volume of DPBS (30 mls) was added to the blood. The diluted blood was placed into a 50 ml centrifuge tube, and 14 ml of Percoll (1.087 g/ml) was pipetted under the blood. This was then centrifuged for 30 min at 1800 RPM.

The top plasma layer was discarded and the cell layer at the interface was removed and placed into a clean 50 ml centrifuge tube. DPBS (Dulbecco's Phosphate Buffered Saline) was added to a total volume of 50 ml and the preparation was centrifuged at 1400 RPM for 10 min at room temperature. The supernatant was removed and the cell pellet was placed in a clean tube and resuspended in 25 ml of IMDM medium with 10% fetal bovine serum. The resuspended cells were then placed on a 150 mm glass petri plate which had been incubated for 1 hour with fetal bovine serum. The cells were incubated on the petri plate for 1.5–2 hours at 37 degrees in a humidified $CO_2$ incubator.

After the incubation, the medium was aspirated off and the attached cells were washed 3 times in the petri dish with DPBS. The attached cells were then scraped off in 10 mls of DPBS and transferred to a clean 50 ml centrifuge tube. The volume of DPBS was increased to 50 mls, and the cells were centrifuged at 1200 RPM for 10 minutes. After centrifugation, the cell pellet was resuspended in 25 ml of medium and transferred to a T75 flask. The cells were then grown at 37 C in a humidified CO2 incubator. From each 30 ml of blood, two T75 flasks were plated with macrophages.

3) MHRV propagation: Frozen tissue from LL, the patient with mantle cell lymphoma (MCL-1), was frozen and thawed three times and lysate (approx. $10^7$ cells) was added to a T75 flask of macrophages 1 to 2 days after they were plated. The lysate was added directly to the medium over the cells, and incubated with the cells for 24 hours. After the incubation period, the cells were washed with DPBS and then 15 mls of medium was placed over the cells. Medium was changed weekly.

To obtain material for MHRV propagation, the medium was aspirated from the cells, 5 ml of fresh medium was added over the cells, and the cells were scraped off of the flask surface using a cell scraper. These cells were then used for analysis, or to introduce the MHRV to new macrophage cultures after freezing and thawing 3–4 times. Cell free supernatants from productively infected primary co-cultures were also successfully used for MHRV transmission after filtration through a 0.22 micron filter.

4) Sample preparation and storage: Cell culture supernatants were replaced weekly and stored at −80° C. until analyzed. Scraped cells were stored in liquid nitrogen until used for analysis or for propagation.

5) Cell growth and maintenance: Cells were grown in medium composed of (1) 50% Myelocult H5100 (Stem Cell Technologies), (2) 25% IMDM (Biowhittaker) supplemented with 10% fetal bovine serum (Hyclone), glutamine (Biowhittaker), and a Pen-strep solution (Biowhittaker), (3) 25% IMDM conditioned medium which had been incubated in a flask containing confluent human diploid fibroblasts. The medium was supplemented with M-CSF (1 microgram/ml, Sigma), IL-3 (1 micrograms/ml, Sigma), and an antibiotic-antimycotic supplement (Life Science Technologies).

6) Experimental samples: After preparation of the macrophage cultures, the cells were exposed to lysates containing the MHRV for 24 hours. The medium was then removed from over the cells approximately once a week, and stored at −80° C. At the end of the experiment, which was between 6 and 8 weeks, the cell monolayers were scraped off of the flasks and frozen in 10% DMSO/medium in liquid $N_2$. These cells were used for electron microscopy.

Figure 5:
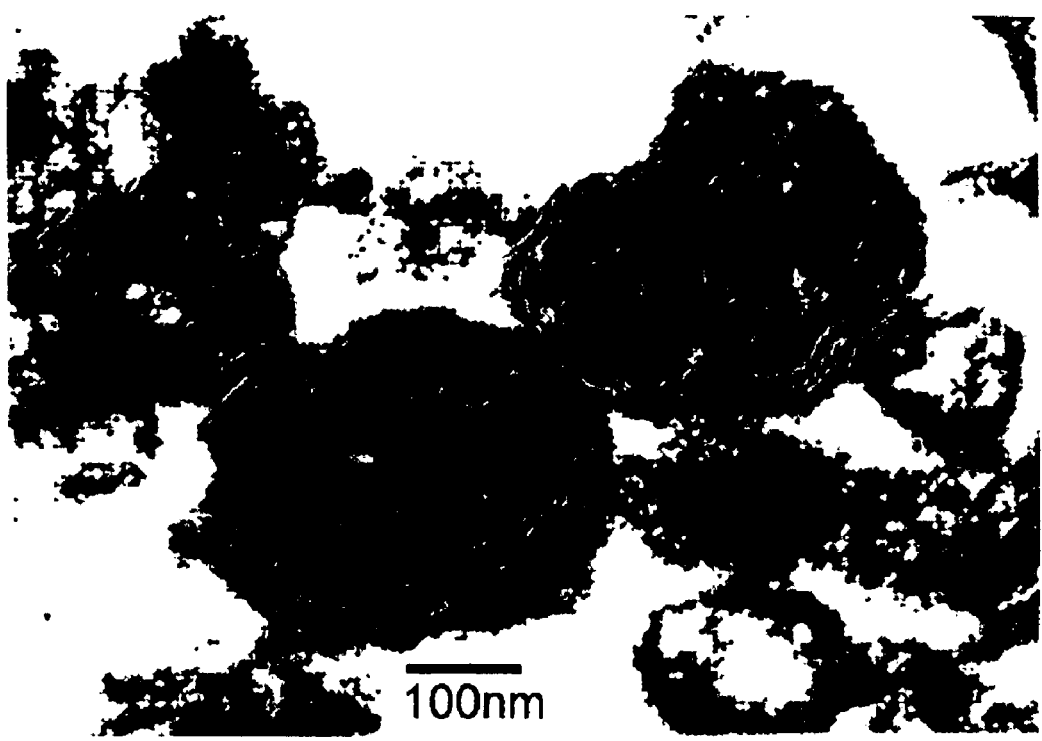
FIG. 5 is a photograph of a transmission electron microscopy image of MHRV in infected macrophages.

Electron microscopy of MHRV infected primary macrophages: Transmission electron microscopy was performed on cells infected with MHRV for 1 month as described above. In the majority of cases where retroviral particles were observed, they were present in intracellular vacuoles and had characteristic morphology of a B/D type retrovirus. The classical morphology reproducibly observed for this retrovirus is shown in FIG. 5. No similar particles were observed in parallel uninfected macrophage cultures from the same primary macrophage donors.

Example 3

Cloning of MHRV

Figure 6:
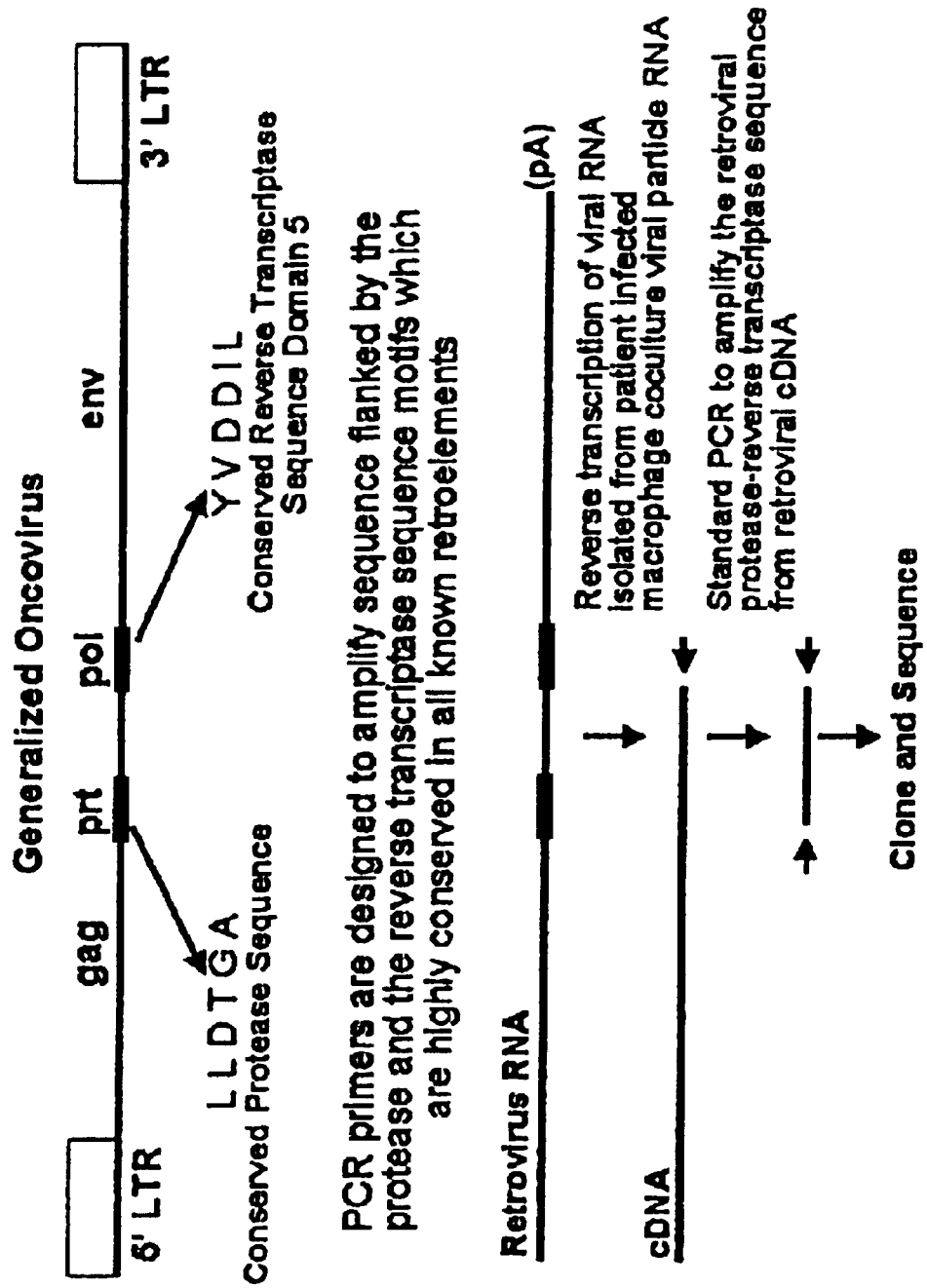
FIG. 6 is a schematic detailing the strategy used to clone the MHRV genome.

The cloning strategy used to clone the MHRV genome is provided in FIG. 6. After sequencing of the initial pol protease gene fragment according to methods well known in the art, a homology search was performed and both the protease (pro) and the polymerase (pol) gene were found to have complete open reading frames encoding intact proteins similar to those previously described for the human endogenous retrovirus-K subfamily of viruses. The initial closest homology was related to the HERV-K109 virus.

The subsequent cloning strategy employed MHRV specific primers extending both 5-prime and 3-prime from the initial pol protease gene. This strategy yielded stretches of DNA encoding for the entire length of the virion. BLAST analysis revealed that the MHRV sequence had the highest homology with the HERV-K109 genome. Virtual complete homology was observed at the 5' end in the pol gene, but with a heterologous region present in the gag region Open reading frame analysis using the ORF finder tool (NCBI) of the MHRV genome sequence revealed an open reading frame encoding the MHRV GAG protein. The nucleotide sequence (SEQ ID NO:7) and predicted amino acid sequence (SEQ ID NO:8) of the 5' end of the GAG gene are as follows:

```
1301 atggtttccagaacaaggaactttagatctaaaagaagact
      M  V  S  R  T  R  N  F  R  S  K  R  R  L ggaa
                                            E
```

-continued

```
1346 aagaattggcaaggaactaaagcaggtaggaagggtaatat
      K  N  W  Q  G  T  K  A  G  R  K  G  N  I catt
                                              I 1391 ccacttacagtatggaatgattgggccattattaaagcagc
      P  L  T  V  W  N  D  W  A  T  I  K  A  A ttta
                                               L 1436 gaaccatttcaaagagaagaagatagtgtttcagtttctga
      E  P  F  Q  R  E  E  D  S  V  S  V  S  D tgcc
                                               A 1481 cctggaagctgtgtaatagattgtaaagacaagacagggaa
      P  G  S  C  V  I  D  C  K  D  K  T  G  K aaaa
                                               K 1526 tcccagaaagaaacggaaagtttacattgcaaatatgtagc
      S  Q  K  E  T  E  S  L  H  C  K  Y  V  A agag
                                               E 1571 ccagtaatggctcagtcaacgcaaaatgttgactataatca
      P  V  M  A  Q  S  T  Q  N  V  D  Y  N  Q atca
                                               S 1616 attacaggggttgatatatcc                     1636
      I  T  G  V  D  I  S
```

The nucleotide residue numbering is based on the position of the nucleotide within the preliminary MHRV genomic sequence (1–9182). The 5' end of the 304 bp PCR product is found within this sequence, beginning at nucleotide residue 1325 using the numbering set out above. These sequences are referred to herein as the MHRV 5" GAG nucleic acid and polypeptide sequences.

Figure 1:
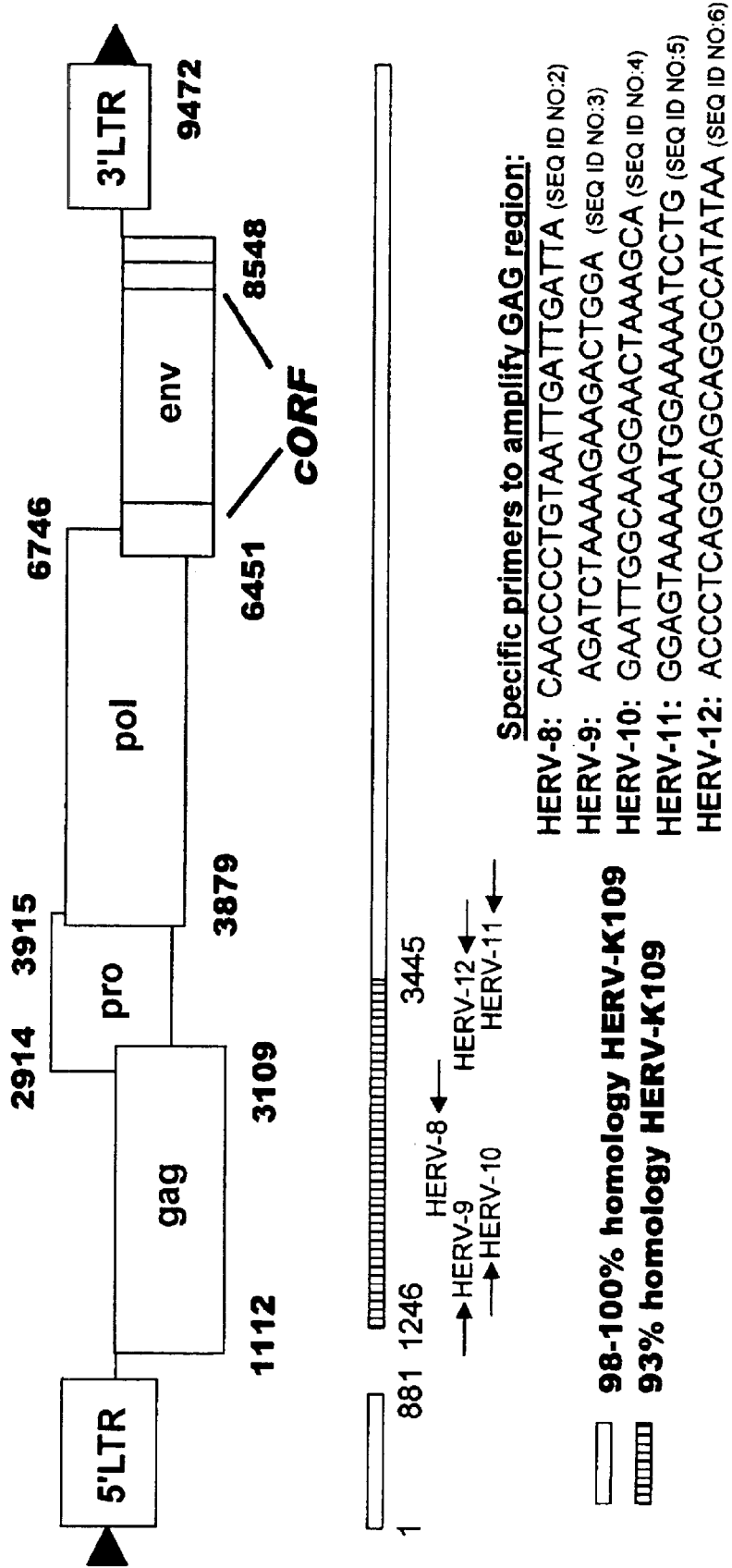
Figure 2:
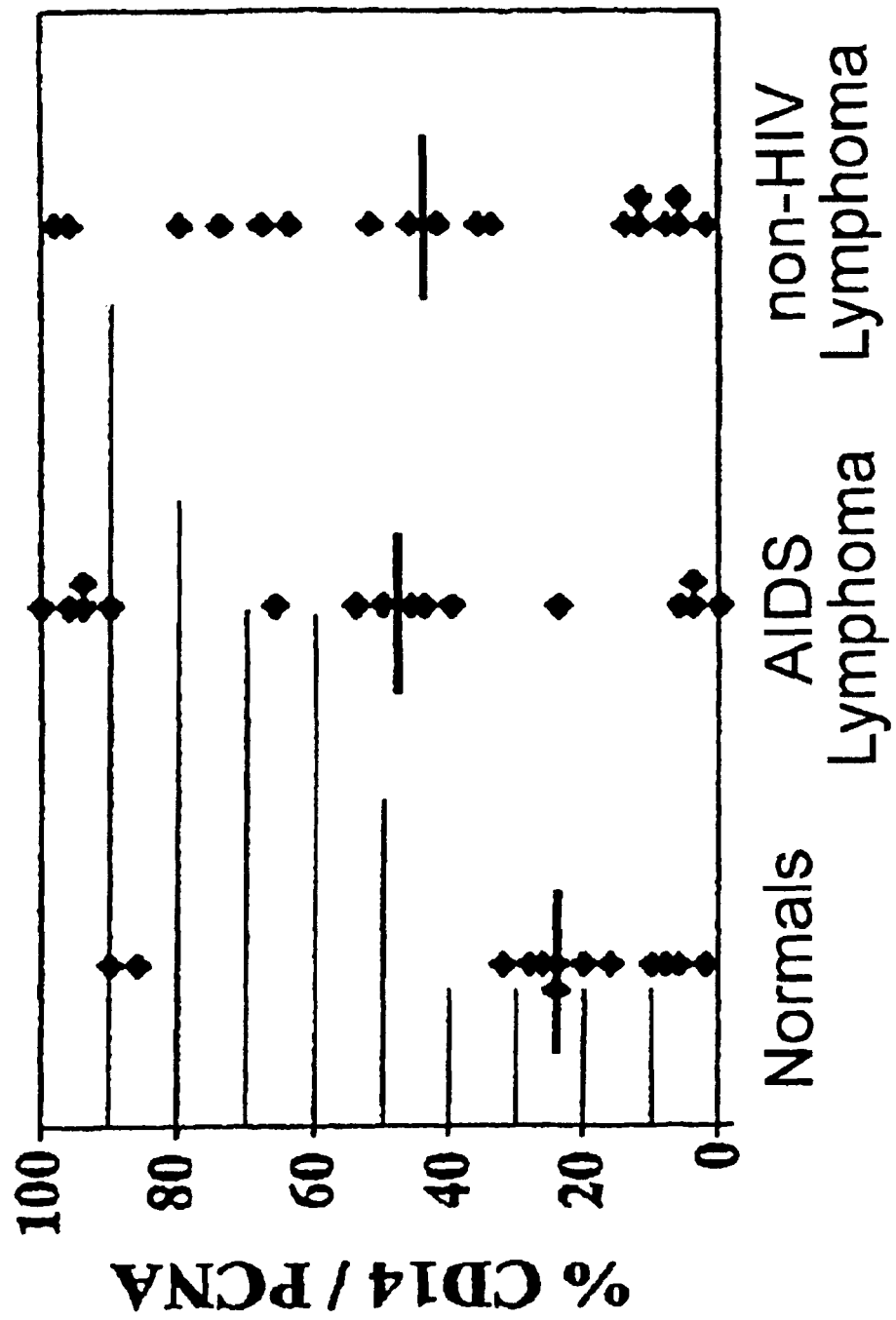
FIG. 2 is a graph showing the levels of PCNA in peripheral blood mononuclear cells isolated from control (Normals), AIDS lymphoma (HIV-non-Hodgkin's lymphoma), and non-HIV lymphoma subjects.
Figure 3:
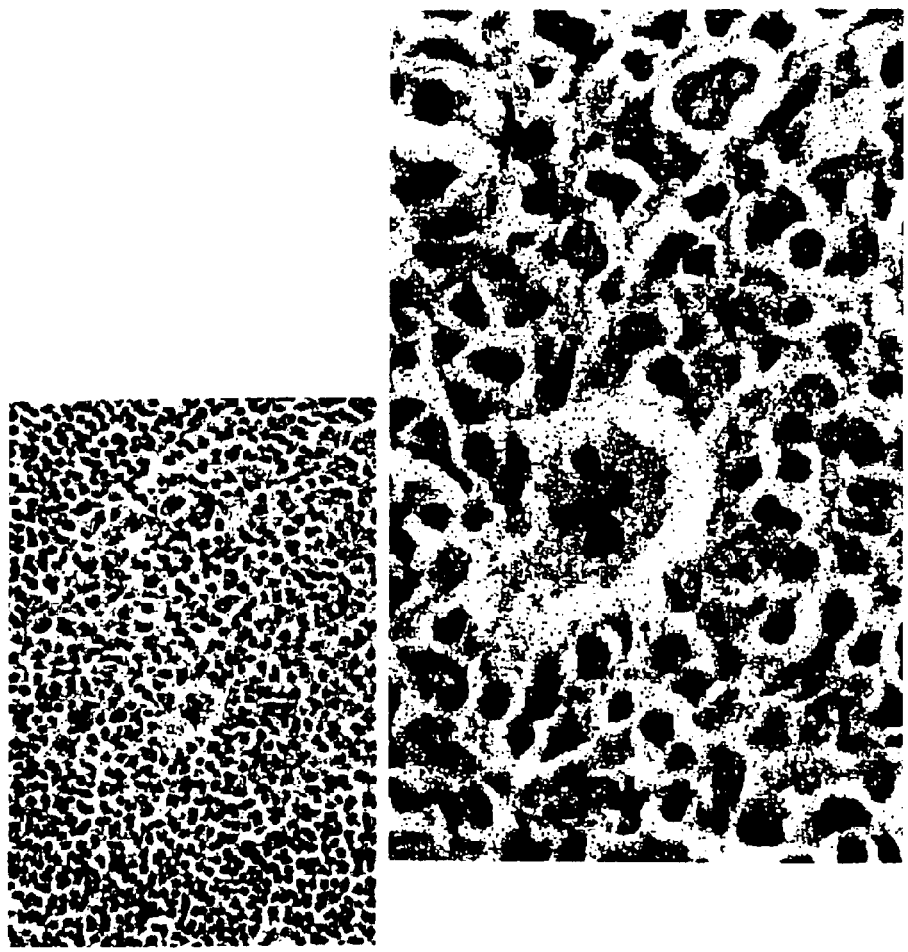
FIG. 3 is a photograph showing a follicular lymphoma with atypical mitotic figure in presumed follicular dendritic cells in a subject having a non-HIV lymphoma.

The homologies related to the HERV-K109 are shown in FIG. 1. A High degree of homology was observed between the MHRV genome and the HERV-K109 genome after about nucleotide residue 3548 of the MHRV genome, with a significant degree of non-homology occurring just 5' to this region and encompassing the entire gag gene of the MHRV. Sequence analysis of the MHRV gag gene did not reveal any greater homology than the observed 93% homology with the HERV-K109 gag gene. Other viral gag elements similar to this region all fell within the HERV family, but were, however, much more distantly related than the HERV-K109. The sequence of the MHRV genome thus suggests a possible recombinational event between an unknown gag-containing exogenous retroviral element and HERV-K109, with subsequent production of an infectious retrovirus. Large open reading frames were present for all genes (gag, pol, env) required for viral replication.

Example 4

MHRV DNA is Detected in the Original Mantle Cell Lymphoma DNA, but not in DNA Isolated from either Normal Donors or an HIV+AIDS Lymphoma DNA Specimen In order to test whether the MHRV would be a candidate unique virus present in the original mantle cell lymphoma, primers were constructed based on unique gag gene sequences and utilized to amplify DNA specimens prepared from the original mantle cell lymphoma DNA or DNA from a patient with AIDS related lymphoma. The sequence of the primers used (HERV-8, HERV-9, HERV-10, HERV-11, and HERV-12) are provided in FIG. 1. Amplification using the HERV-10 and HERV-11 primer pair (samples A and B, lane 3 of FIG. 7) should result in production of a PCR product of approximately 1966 bp; amplification using the HERV-9 and HERV-12 primer pair (samples A and B, lane 2 of FIG. 7) should result in an approximately 1321 bp PCR product; and amplification using the HERV-8 and HERV-9 primer pair (samples A and B, lane 1 of FIG. 7) should result in an approximately 304 bp PCR product. PCR amplification was carried out using DNA isolated from the original mantle cell lymphoma (MCL-1 DNA) and from an AIDS-Non-Hodgkin's lymphoma (AIDS-NHL DNA). PCR was carried out according to methods well known in the art, with a Tm of 65° C. Specifically, a DNA sample in 2 µl (in the range of about 100 ng DNA or less) was incubated in 5 µl 10×buffer, with 1 µl of 200 µM dNTP, 3 µl 1.5 mM MgCl$_2$, 1 µl of each of the primers (each at 400 nM), and 0.3 µl of 1.5 µM AmpliTaq DNA Polymerase, with 36.7 µl water. The PCR cycles were as follows 3 min at 94° C.; 40 cycles of 30 sec at 94° C. followed by 1 min at 65° C.; 2 min at 68° C.; and 10 min at 68° C.

FIG. 7 shows the results of this analysis. As shown in lanes 1–3 (B, MCL-1 DNA), the three sets of gag-specific PCR primers all yielded specific gene products of a molecular weight as predicted based on the initial MHRV sequencing analysis. These sizes are shown on the right axis. The same sets of primers failed to amplify anything from DNA isolated from an HIV+AIDS lymphoma DNA (A, AIDS-NHL DNA). The HERV-8/-9 primer pair failed to amplify any detectable PCR product form the HIV+AIDS lymphoma DNA; a faint band was present using the HERV-9/-12 primer pair, and no full-length (1966 bp) PCR product was detected using the HERV-10/-11 primer pair (A, 1–3). Therefore MHRV specific primers did not detect sequence present in the normal human genome (A lanes). These data are consistent with detection of MHRV specifically from DNA in the patient's original tumor (B lanes).

Subsequent studies on blood specimens from this patient at a time when the lymphoma was in remission revealed MHRV specific DNA of the same sizes as described in FIG. 7. These data indicate that MHRV is present within the original tumor, and does not require the presence of tumor cells in order to be observed in blood specimens.

Example 5

Analysis of the MHRV GAG Sequence

The MHRV full-length GAG polypeptide sequence described in Example 3 above was used as a query sequence (SEQ ID NO:9) in a BLAST analysis of GenBank. Exemplary results GenBank Accession Nos. AF164609 (SEQ ID NO:10) and Y08032 (SEQ ID NO:11) are shown below.

```
>gb|AAD51791.1| (AF164609) Gag-Pro-Pal protein [Homo sapiens]
Length = 1177; Score = 162 bits (409), Expect = 4e-39
Identities = 79/100 (79%), Positives = 88/100 (88%), Gaps = 2/100 (2%)
Query:    5 TRNFRSKRRLEKNWQGTKAGRKGNIIPLTVWNDWAIIKAALEPFQREEDSVSVSDAPGSC    64
            T + +   +R+ K   + +AGRKGNIIPLTVWNDWAIIKAALEPFQ EEDSVSVSDAPGSC
Sbjct:   54 TLDLKDWKRIGKELK--QAGRKGNIIPLTVWNDWAIIKAALEPFQTEEDSVSVSDAPGSC   111

Query:   65 VIDCKDTGKKSQKETESLHCKYVAEPVMAQSTQNVDYNQ                      104
            +IDC +KT KKSQKETESLHC+YVAEPVMAQSTQNVDYNQ
Sbjct:  112 IIDCNEKTRKKSQKETESLHCEYVAEPVMAQSTQNVDYNQ                     151

>emb|CAA69289.1| (Y08032) gag [Human endogenous retrovirus K]
Length = 666; Score = 161 bits (407) , Expect = 6e-39
Identities = 79/100 (79%), Positives = 88/100 (88%), Gaps =2/100 (2%)
Query:    5 TRNFRSKRRLEKNWQGTKAGRKGNIIPLTVWNDWAIIKAALEPFQREEDSVSVSDAPGSC    64
            T + +   +R+ K   + +AGRKGNIIPLTVWNDWAIIKAALEPFQ EEDSVSVSDAPGSC
Sbjct:   54 TLDLKDWKRIGKELK--QAGRKGNIIPLTVWNDWAIIKAALEPFQTEEDSVSVSDAPGSC   111

Query:   65 VIDCKDTGKKSQKETESLHCKYVAEPVMAQSTQNVDYNQ                      104
            +IDC +KT KKSQKETESLHC+YVAEPVMAQSTQNVDYNQ
Sbjct:  112 LIDCNEKTRKKSQKETESLHCEYVAEPVMAQSTQNVDYNQ                     151
```

In each instance, no polypeptide matched the first four amino acids of the query MHRV GAG amino acid sequence. The N-terminal portion up to and including residue 22 of the MHRV GAG polypeptide showed little homology to known gag polypeptides.

Example 6

Macrophages Infected with MHRV Produce Intact Viral Particles

In order to test whether in vitro infection of primary macrophages with MHRV would yield viral particles, the following experiments were performed in accordance with the methods described above. Primary macrophage donors were infected with MHRV with parallel cultures of the same cells left uninfected. Methods were followed as above.

At 6 weeks after the initiation of infection, supernatants were obtained from the infected and uninfected cultures, debris pelleted, and the supernatant layered over a 25/45% sucrose step gradient. Ultracentrifugation was performed at 90,000 G for 2 hours, and the gradient was fractionated into 4 sections. The upper medium containing section (A and B, lane 1, FIG. 8), the 25% sucrose section (A and B, lane2, FIG. 8), the 25/45% banded material (A and B, lane 3, FIG. 8), and the pellet (A and B, lane 4, FIG. 8) were all treated with DNAseI and RNA was extracted. The same procedure was followed for supernatants from both infected and uninfected cells. MHRV specific primers (HERV-K8 and HERV-K9) were utilized in a reverse transcriptase PCR experiment on each of the gradient selected specimens.

As shown in FIG. 8, only the specimen from the MHRV infected culture 25/45% interface contained MHRV specific RNA as detected. There was no detectable MHRV particle associated RNA in any of the other fractions from the infected supernatant, neither were there detectable, amplifiable sequences from the uninfected control supernatants. These data are consistent with the detection of particle associated MHRV RNA produced by primary macrophages infected 6 weeks prior to analysis with a source of MHRV. Similar experiments have been performed in 8 different primary macrophage donors with a confirmation of infection provided by electron microscopy showing the existence of viral particles within cells similar to those shown in FIG. 5.

The ability of isolated MHRV to infect cells in vitro suggest that the virus is likely to be transmissible in blood, and thus screening of the blood supply (including blood products such as plasma and serum) for MHRV is warranted, as is the screening of tissues and other biological materials that may contain MHRV infectious nucleic acid.

Example 7

Western Blot Analysis of MHRV

In order to test whether the original mantle cell lymphoma patient had shown an immunologic response against the MHRV specific proteins, plasma was obtained from this patient at a time when the patient was in complete remission (after bone marrow transplant). This plasma was a source of antibodies for testing against cell lysates obtained from infected and uninfected cells (as described above) to determine whether any MHRV specific proteins could be observed. Western blot was performed according to methods well known in the art.

Aliquots ($2 \times 10^6$ cells) of infected and non-infected normal donor peripheral blood derived macrophages were boiled for 4 minutes in 0.5 ml of sample buffer (62.5 micromolar Tris-HCI, pH 6.8, with glycerol 25%, SDS, 2% and 0.01% bromophenol blue). 30 microliters of sample were loaded into 4–15% polyacrylamide gels (BIO-RAD, Richmond, Calif.) and processed essentially according to methods previously described (Ng et al. *J Immunol* 143:2501–2507 (1989)). Briefly, samples were run at 100 v for 1 hour in 25 micromolar Tris, 192 micromolar glycine, 0.1% SDS, pH 8.3. Proteins were transferred to nitrocellulose (Scheicher & Schuell, Keene, N.H.) for 1 hour at 90 volts in 25 micromolar Tris, 192 micromolar glycine, 20% methanol transfer buffer. After overnight, 4° C., blocking with 2% milk/PBS, membranes were reacted with 1/100 dilution of patient plasma for 30 minutes, then washed with PBS. Anti-Human IgG alkaline phosphatase in PBS (Zymed, South San Francisco, Calif.) was then added for 30 minutes, then blots were washed with PBS. Detection of biotin-molecular weight markers (BIO-RAD) was accomplished by incubation with avidin-AP (Zymed). Detection of protein-antibody bands was by addition BCIP/NBT substrate (Zymed).

FIG. 9 shows a preliminary Western blot result showing specific bands present in infected as compared to uninfected primary macrophages. The samples are ordered as follows, from left to right: infected cell lysate plus the detectably labeled secondary antibody anti-IgG-AP (C (for control), MHRV infected); infected cell lysate, patient plasma, and anti-IgG-AP (LL); anti-IgG-AP and uninfected cells (C, MHRV uninfected); and uninfected cells, patient plasma (LL), and anti-IgG-AP (LL, MHRV uninfected).

The patient plasma only reacted with the MHRV infected cells. The size of the observed protein bands (68 kD and 80 kD) may be due to glycosylation of the protein. Since the immune response in patients several months post bone marrow transplant is generally all T cell independent, the Western blot bands observed are likely to be the glycosylated forms (i.e., envelope) of MHRV proteins.

Example 8

Viral Cultivation

MHRV is isolated from frozen and/or fresh tissues in the same manner as described above. After cocultivation of primary tumor material/blood derived CD14+(from cell sorting) for 1 month, adherent macrophages are scraped from the tissue culture flask, pelleted and prepared for electron microscopic analysis. Supernatants from those cells are frozen and evaluated for the presence of particle associated DNA-ase resistant RNA that bands at a sucrose density in a step gradient of 25–45% sucrose. Primers utilized for identification of MHRV representing universal protease and polymerase degenerative primer sets are used to identify the presence of particle associated virions as described in FIG. 1. Supernatant is isolated from any coculture that yields a positive result, the supernatant filtered through a 0.22 micron filter, and primary cultures reinoculated followed by a 1 month culture. The same EM and viral RNA characteristics are scored prior to further characterization/cloning of a potential novel retroviral element.

Example 9

Molecular Epidemiology using MHRV-Based Sequences

Because the MHRV gag gene has unique sequences which have allowed the development of specific PCR primer sets recognizing only MHRV, a molecular epidemiology study is performed to identify MHRV specific sequences in blood from patients with a broad range of chronic disease states. Other novel retroviral agents as they are discovered will be characterized in a manner similar to characterization studies as defined below for MHRV.

Source of patient material: Patient derived specimens are evaluated for the presence of MHRV specific sequences and/or antibody reactivities. The initial focus of molecular epidemiological studies is the evaluation of a series of lymphoma patient tissues as well as blood cells derived from those patients for the presence of MHRV specific sequences. A broader study on the role of MHRV and its transmission capabilities is performed if MHRV specific sequences are identified within subsets of patients with lymphoma.

Other classes of specimen evaluated for MHRV specific sequences will include diseases which have been associated with finding HERV specific sequences in a variety of publications over the past 10 years. These include specimens from patients with multiple sclerosis, teratocarcinoma, breast cancer, and a variety of autoimmune diseases. All of these classes of material are currently available; tissue, where available, as well as PBMCs is evaluated for the presence of MHRV specific sequences. Control specimens from normal donors are obtained through a blood bank. After analysis of the results of this initial screen, further control specimens from other disease states are evaluated. These primary pathologic tissues will also serve as a source of potential other MHRV related sequences, which are cloned and sequenced so as to determine degree of MHRV heterogeneity within different chronic disease settings.

Example 10

Characterization of MHRV Growth Characteristics in Vitro

MHRV which was initially isolated from a primary mantle cell lymphoma tumor tissue. Expression appeared exclusively related to tumor associated macrophages (electron microscopy, not shown) was initially isolated in primary macrophage cultures in vitro. As discussed above, only infected cultures showed evidence for MHRV specific sequence production in particle associated RNA isolation sucrose banding assays. This assay allows differentiation between actual virion associated packaged MHRV sequences as compared to contaminating endogenous retroviral RNAs, which are not typically packaged into intact viral particles.

A detailed host range analysis of MHRV in a variety of cell types is performed. Host range studies include the use of primary cultured macrophages as a positive control, with attempts to infect a variety of tumor cell lines of human origin, normal cells (lymphocytes, fibroblasts, endothelial cells) and a variety of animal cell populations including mouse, rat, rabbit, bovine, as well as any other cell lines of different animal species should MHRV replicate in any non-human cell population.

An ultimate goal is to determine whether MHRV can infect non-human cells in order to develop a disease model for future study. MHRV viral production is monitored by tracking viral specific gag sequences by PCR. For in vitro propagation purposes, MHRV will continue to be grown in primary human macrophages and all virus isolation studies will be performed on infected vs. uninfected macrophages from the same donor with preparations processed in parallel so as to track MHRV specific proteins during purification processes.

Example 11

Characterization of MHRV Proteins

MHRV is highly related to human endogenous retrovirus. The study of MHRV specific proteins will yield the first view of what a potential replication competent human endogenous retrovirus protein profile could look like. As discussed above, open reading frames were observed in the HERV-K109 related protease, polymerase, and envelope genes.

MHRV produced in chronically infected macrophages are labeled with radioactive amino acids, and retroviruses produced by those cells isolated through sucrose gradient purification techniques. MHRV-specific proteins are visualized utilizing 2-dimensional gel electrophoresis with particle associated radioactive proteins from uninfected cells of the same donors serving as nonspecific control.

This will provide visualization of mature retroviral protein products from MHRV, and will also serve as a map for studying antibody reactivity in patients infected with MHRV (detected by DNA PCR amplification studies using MHRV specific primers) as compared to patients who are infected with a variety of other retroviruses such as HIV or HTLV-1 or simply have antibodies with broadly cross-reactive capabilities (such as patients with a variety of autoimmune diseases). This approach can also serve as a potential purification scheme for native retroviral proteins with their post-transcriptional/translational modifications as they occur in a package replication competent form.

Example 12

Detection of MHRV in Lymphomas

Using the 304 base pair primers DNA was amplified from a series of specimens isolated from patients as described above. The following were negative:
a) 6 normal macrophage cultures, all uninfected, from different normal blood bank donors(Stanford);
b) 2 AIDS lymphoma tissues and their uninvolved spleens (4 specimens);
c) 4 normal peripheral blood DNA preparations, HIV negative; and
d) 2 non AIDS follicular lymphomas.

Five specimen were positive, as follows:
1) MT: AIDS ascites large cell lymphoma;
2) S93–268102: Non AIDS follicular lymphoma;
3) UV: The original MHRV RNA sequence;
4) S92–4336: Non-AIDS follicular lymphoma; and
5) BR: AIDS large cell lymphoma.

Notably, the MT lymphoma (1) immediately above) was previously used to establish high grade lymphomas in SCID mice by use of sorted CD14 cells; mouse lymphoma cells expanded in vivo, driven in part by the MT (MHRV+) lymphoma macrophages.

The amplified GAG sequence from each of 1–5 above was sequenced, and the sequences compared to that of the MHRV GAG (UV). The sequence of the MHRV GAG of the LL tissue represents the mantle cell lymphoma tissue DNA in which MHRV was originally identified. The alignment of the sequences are provided in FIG. 10.

The DNA sequence of the 304 bp PCR product of the LL tissue, the MT lymphoma, and the S93–268102 were identical. The DNA sequences of the 304 bp PCR product of the UV, S92–4336, and BR isolates each differ from the LL sequence by one nucleotide (nucleotide 232 of the 304 segment(G to A); nucleotide 89 (nucleotide 89, G to A); and nucleotide 168 (T to C), respectively.

These data indicate that MHRV is a human lymphoma associated virus, containing unique genetic sequences conserved between individual tumor associated isolates.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An isolated mantle histiocyte retrovirus (MHRV) particle.

2. The isolated MHRV particle of claim 1, comprising an RNA genome encoding a GAG polypeptide comprising an amino acid sequence of amino acid residues 1–22 of SEQ ID NO:8.

3. The isolated MHRV particle of claim 1, comprising an RNA genome wherein PCR amplification of the RNA genome using a first primer comprising SEQ ID NO:2 and a second primer comprising SEQ ID NO:3 produces an amplification product of about 304 bp.

4. The isolated MHRV particle of claim 3, wherein the 304 bp amplification product comprises the sequence of SEQ ID NO:1 or a complement thereof.

5. The isolated MHRV particle of claim 1, wherein the particle contains an RNA genome that, following infection and activity of viral reverse transcriptase, generates a cDNA that hybridizes under conditions of high stringency to a nucleic acid sequence of SEQ ID NO:1 or a complement thereof.

6. The isolated MHRV particle of claim 1 comprising an RNA molecule comprising a sequence corresponding to SEQ ID NO:1 or a complement thereof.

7. An isolated MHRV particle wherein the particle:
   is isolatable from a human lymphoma;
   has a particle diameter of from about 90 nm to 110 nm;
   has a membrane lipid bilayer;
   has an RNA genome visible by electron microscopy as a conical eccentric nucleoid; and
   has a GAG envelope polypeptide comprising amino acid residues 1–22 of the amino acid sequence of SEQ ID NO:8.

8. An isolated MHRV particle wherein the particle:
   is isolatable from a human lymphoma;
   has a particle diameter of from about 90 nm to 110 nm;
   has a membrane lipid bilayer; and
   has an RNA genome visible by electron microscopy as a conical eccentric nucleoid; and
   wherein the RNA genome comprises a nucleic acid sequence corresponding to nucleotide residues 1–66 of SEQ ID NO:7 or a complement thereof.

9. An isolated mammalian cell infected with the virus of claim 1.

10. The isolated mammalian cell of claim 9, wherein the cell is a macrophage.

11. An isolated mammalian cell infected with the virus of claim 8.

12. The isolated mammalian cell of claim 11, wherein the cell is a macrophage.

13. The isolated mammalian macrophage of claim 10 or 12, wherein the macrophage produces MHRV particles.

14. An isolated polynucleotide comprising a sequence encoding a polypeptide comprising an amino acid sequence of at least 4 contiguous amino acid residues of amino acid residues 1–22 of SEQ ID NO:8.

15. The isolated polynucleotide of claim 14, wherein the polynucleotide comprises a sequence encoding a polypeptide comprising an amino acid sequence of at least 10 contiguous amino acid residues of amino acid residues 1–22 of SEQ ID NO:8.

16. An isolated polynucleotide comprising a sequence of at least 12 contiguous residues of nucleic acid residues 1–66 of SEQ ID NO:7 or a complement thereof.

17. The isolated polynucleotide of claim 16, wherein the polynucleotide comprises a sequence of at least 33 contiguous residues of nucleic acid residues 1–66 of SEQ ID NO:7 or a complement thereof.

18. The isolated polynucleotide of claim 17, wherein the polynucleotide comprises a sequence of at least 50 contiguous residues of nucleic acid residues 1–66 of SEQ ID NO:7 or a complement thereof.

19. The isolated polynucleotide of claims 14–18, wherein the polynucleotide is less than about 1 kb in length.

20. The isolated polynucleotide of claims 14–18, wherein the polynucleotide is operably linked to a heterologous promoter element.

21. An isolated polynucleotide comprising a sequence that hybridizes under conditions of high stringency to the polynucleotide sequence of nucleotides 1–66 of SEQ ID NO: or a complement thereof 7.

22. An isolated polynucleotide comprising a sequence having at least 65% identity to at least 12 contiguous nucleotides of nucleic acid residues 1–66 of SEQ ID NO:7 or a complement thereof.

23. An isolated recombinant host cell containing the polynucleotide of any of claims 14 to 22.

24. An isolated vector containing the polynucleotide of any of claims 14 to 22.

25. An isolated MHRV GAG polypeptide.

26. An isolated polypeptide encoded by the polynucleotide of any of claims 14 to 22.

27. An isolated antibody that specifically binds the isolated MHRV GAG polypeptide of claim 25.

28. An isolated antibody that specifically binds the a polypeptide encoded by the polynucleotide of any of claims 14 to 22.

29. A method for detecting mantle histiocyte retrovirus (MHRV) in a sample, the method comprising:
   contacting a biological sample suspected of containing MHRV with an MHRV-specific probe, said contacting being for a time sufficient for binding of the MHRV-specific probe to the sample to form complexes between the probe and a probe target; and
   detecting the presence or absence of complexes of the MHRV-specific probe and the probe target in the sample;
   wherein detection of complexes in the sample indicates MHRV is present in the sample.

30. The method of claim 29, wherein the MHRV-specific probe and the probe target are nucleic acid, and wherein the MHRV-specific probe comprises at least 8 contiguous nucleotide residues of SEQ ID NO:1 or a complement thereof.

31. The method of claim 29, wherein the MHRV-specific probe and the probe target are nucleic acid, and wherein the MHRV-specific probe comprises at least 8 contiguous nucleotide residues of residues 1–66 of SEQ ID NO:7 or a complement thereof.

32. The method of claim 29, wherein the MHRV-specific probe is an MHRV-specific antibody and the probe target is an MHRV GAG polypeptide.

33. The method of claim 29, wherein the probe target is an anti-MHRV antibody and the MHRV-specific probe is a polypeptide comprising amino acid residues 1–22 of SEQ ID NO:8.

34. The method of claim 29, wherein the biological sample is blood, blood-derived products, plasma, or serum.

35. The method of claim 29, wherein the biological sample comprises a tissue containing a macrophage or a macrophage-derived tumor cell.

36. A method for detecting a mantle histiocyte retrovirus (MHRV) in a sample, the method comprising:
   contacting a biological sample suspected of containing MHRV with a first MHRV-specific nucleic acid probe and with a second MHRV-specific nucleic acid probe, wherein the first probe and the second probe each comprise at least 15 contiguous nucleotides of a nucleic acid sequence of SEQ ID NO:7 or a complement thereof, said contacting being under conditions effective to produce an amplified DNA product; and detecting the presence or absence amplified DNA product;

wherein detection of amplified DNA product corresponding to an amplified DNA product expected from a nucleic acid sequence comprising SEQ ID NO:7 or a complement thereof indicates the MHRV is present in the sample.

37. The method of claim 36, wherein the first probe comprises a sequence of HERV-9 (SEQ ID NO:3) or HERV-10 (SEQ ID NO:4).

38. The method of claim 36, wherein the second probe comprises a sequence of HERV-8 (SEQ ID NO:2), HERV-11 (SEQ ID NO:5) or HERV-12 (SEQ ID NO:6).

39. The method of claim 36, wherein the first probe is HERV-8 (SEQ ID NO:2), the second probe is HERV-9 (SEQ IDNO: 3), wherein detection of an amplified product of about 304 bp indicates MHRV is in the sample.

40. The method of claim 36, wherein the first probe is HERV-9 (SEQ ID NO:3), the second probe is HERV-12 (SEQ ID NO:6), wherein detection of an amplified product of about 1321 bp indicates MHRV is in the sample.

41. The method of claim 36, wherein the first probe is HERV-1 (SEQ ID NO:4) the second probe is HERV-11 (SEQ ID NO:5), wherein detection of an amplified product of about 1966 bp indicates MHRV is in the sample.

42. A kit for detection of mantle histiocyte retrovirus (MHRV), the kit comprising an MHRV-specific probe, wherein the probe is:

an MHRV-specific nucleic acid probe that specifically hybridizes to a sequence encoding an MHRV GAG polypeptide;

an MHRV-specific GAG antibody; or an MHRV polypeptide that specifically binds an anti-MHRV GAG antibody.

43. A method of screening for anti-MHRV antiviral agents, the method comprising:

contacting a candidate agent with a culture comprising a mammalian cell infected with MHRV, which cell produces viral particles; and detecting MHRV viral particles in supernatant of the culture;

wherein a decrease in MHRV viral particles in the supernatant indicates that the candidate agent as activity as an anti-MHRV antiviral agent.

44. A method for detecting an MHRV-associated disease, the method comprising:

contacting a biological sample with an MHRV-specific probe, wherein the biological sample was obtained from a subject suspected of having an MHRV-associated disease, said contacting being for a time sufficient for binding of the MHRV-specific probe to the sample to form complexes between the probe and a probe target; and detecting complexes of the MHRV-specific probe and the probe target in the sample;

wherein detection of complexes in the sample indicates MHRV is present in the sample, which indicates the subject may have an MHRV-associated disease.

45. The method of claim 44, wherein the MHRV-associated disease is an MHRV-associated lymphoma.

46. The method of claim 44, wherein the MHRV-associated disease is teratocarcinoma, multiple sclerosis, autoimmune rheumatic diseases or schizophrenia.

47. A method for producing an MHRV GAG polypeptide of claim 25, the method comprising the steps of:

a) culturing a recombinant host cell containing a recombinant MHRV GAG polypeptide-encoding polynucleotide sequence under conditions suitable for the expression of the polypeptide; and b) recovering the polypeptide from the host cell culture.

48. An immunogenic composition comprising an immunogenic polypeptide, wherein the immunogenic polypeptide comprises an amino acid sequence of amino acid residues 1–22 of a GAG polypeptide of mantle histiocyte retrovirus (MHRV).

49. An immunogenic composition comprising a nucleic acid molecule having a sequence encoding an immunogenic polypeptide, wherein the immunogenic polypeptide comprises an amino acid sequence of amino acid residues 1–22 of a GAG polypeptide of mantle histiocyte retrovirus (MHRV), and wherein the nucleic acid sequence is adapted for expression in a mammalian cell.

50. An isolated recombinant MHRV vector, the vector comprising:

the MHRV polynucleotide of any of claims 14 to 22;

at least one restriction site suitable for insertion of a heterologous nucleic acid; and a nucleic acid of interest comprising a sequence heterologous to the MHRV polynucleotide.

51. The isolated recombinant MHRV vector of claim 50, wherein the restriction site is non-naturally occurring in the MHRV genome.

52. An isolated recombinant MHRV particle comprising:

a recombinant MHRV genome comprising the MHRV polynucleotide of any of claims 14 to 22 and further comprising at least one restriction site suitable for insertion of a heterologous nucleic acid.

53. The isolated recombinant MHRV particle of claim 52, wherein the recombinant MHRV genome further comprises a nucleic acid comprising a sequence heterologous to the MHRV polynucleotide, wherein the nucleic acid is operably inserted for expression in a host upon introduction of the MHRV vector into the host cell.

54. The isolated recombinant MHRV particle of claim 52, wherein the MHRV particle is replication-defective.

55. The isolated recombinant MHRV particle of claim 52, wherein the MHRV particle is replication competent.

56. The method of claim 44, wherein the probe target is a sequence encoding an MHRV GAG polypeptide and the MHRV-specific probe is an MHRV-specific nucleic acid probe that specifically hybridizes to the sequence encoding the MHRV GAG polypeptide.

57. The method of claim 44, wherein the probe target is an MHRV GAG polypeptide and the probe is an MHRV-specific GAG antibody.

58. The method of claim 44, wherein the probe target is an anti-MHRV GAG antibody and the probe is an MHRV polypeptide that specifically binds an anti-MHRV GAG antibody.

* * * * *

SEQUENCE LISTING

```
<160> NUMBER OF SEQ ID NOS: 14
<210> SEQ ID NO 1
<211> LENGTH: 304
<212> TYPE: DNA
<213> ORGANISM: Mantle histiocyte retrovirus

<400> SEQUENCE: 1
agatctaaaa gaagactgga aaagaattgg caaggaacta aagcaggtag gaagggtaat      60
atcattccac ttacagtatg gaatgattgg gccattatta aagcagcttt agaaccattt     120
caaagagaag aagatagtgt ttcagtttct gatgcccctg gaagctgtgt aatagattgt     180
aaagacaaga cagggaaaaa atcccagaaa gaaacggaaa gtttacattg caaatatgta     240
gcagagccag taatggctca gtcaacgcaa aatgttgact ataatcaatc aattacaggg     300
gttg                                                                  304

<210> SEQ ID NO 2
<211> LENGTH: 23
<212> TYPE: DNA
<213> ORGANISM: Artificial Sequence
<220> FEATURE:
<223> OTHER INFORMATION: HERV-8 primer

<400> SEQUENCE: 2
caacccctgt aattgattga tta                                              23

<210> SEQ ID NO 3
<211> LENGTH: 20
<212> TYPE: DNA
<213> ORGANISM: Artificial Sequence
```

```
<220> FEATURE:
<223> OTHER INFORMATION: HERV-9 primer

<400> SEQUENCE: 3
agatctaaaa gaagactgga                                                    20

<210> SEQ ID NO 4
<211> LENGTH: 22
<212> TYPE: DNA
<213> ORGANISM: Artificial Sequence
<220> FEATURE:
<223> OTHER INFORMATION: HERV-10 primer

<400> SEQUENCE: 4
gaattggcaa ggaactaaag ca                                                 22

<210> SEQ ID NO 5
<211> LENGTH: 23
<212> TYPE: DNA
<213> ORGANISM: Artificial Sequence
<220> FEATURE:
<223> OTHER INFORMATION: HERV-11 primer

<400> SEQUENCE: 5
ggagtaaaaa tggaaaaatc ctg                                                23

<210> SEQ ID NO 6
<211> LENGTH: 24
<212> TYPE: DNA
<213> ORGANISM: Artificial Sequence
<220> FEATURE:
<223> OTHER INFORMATION: HERV-12 primer

<400> SEQUENCE: 6
accctcaggc agcaggccat ataa                                               24

<210> SEQ ID NO 7
<211> LENGTH: 336
<212> TYPE: DNA
<213> ORGANISM: Mantle histiocyte retrovirus

<400> SEQUENCE: 7
atggtttcca gaacaaggaa ctttagatct aaaagaagac tggaaaagaa ttggcaagga        60
actaaagcag gtaggaaggg taatatcatt ccacttacag tatggaatga ttgggccatt       120
attaaagcag ctttagaacc atttcaaaga gaagaagata gtgtttcagt ttctgatgcc       180
cctggaagct gtgtaataga ttgtaaagac aagacaggga aaaatcccag aaagaaacg        240 gaaagtttac attgcaaata tgtagcagag ccagtaatgg ctcagtcaac gcaaaatgtt       300
gactataatc aatcaattac agggttgat atatcc                                  336

<210> SEQ ID NO 8
<211> LENGTH: 112
<212> TYPE: PRT
<213> ORGANISM: Mantle histiocyte retrovirus

<400> SEQUENCE: 8

Met Val Ser Arg Thr Arg Asn Phe Arg Ser Lys Arg Arg Leu Glu Lys
  1               5                  10                  15

Asn Trp Gln Gly Thr Lys Ala Gly Arg Lys Gly Asn Ile Ile Pro Leu
                 20                  25                  30

Thr Val Trp Asn Asp Trp Ala Ile Ile Lys Ala Ala Leu Glu Pro Phe
             35                  40                  45
```

```
Gln Arg Glu Glu Asp Ser Val Ser Val Ser Asp Ala Pro Gly Ser Cys
 50                  55                  60

Val Ile Asp Cys Lys Asp Lys Thr Gly Lys Lys Ser Gln Lys Glu Thr
 65                  70                  75                  80

Glu Ser Leu His Cys Lys Tyr Val Ala Glu Pro Val Met Ala Gln Ser
                 85                  90                  95

Thr Gln Asn Val Asp Tyr Asn Gln Ser Ile Thr Gly Val Asp Ile Ser
            100                 105                 110
```

<210> SEQ ID NO 9
<211> LENGTH: 100
<212> TYPE: PRT
<213> ORGANISM: Mantle histiocyte retrovirus

<400> SEQUENCE: 9

```
Thr Arg Asn Phe Arg Ser Lys Arg Arg Leu Glu Lys Asn Trp Gln Gly
  1               5                  10                  15

Thr Lys Ala Gly Arg Lys Gly Asn Ile Ile Pro Leu Thr Val Trp Asn
             20                  25                  30

Asp Trp Ala Ile Ile Lys Ala Ala Leu Glu Pro Phe Gln Arg Glu Glu
         35                  40                  45

Asp Ser Val Ser Val Ser Asp Ala Pro Gly Ser Cys Val Ile Asp Cys
 50                  55                  60

Lys Asp Lys Thr Gly Lys Lys Ser Gln Lys Glu Thr Glu Ser Leu His
 65                  70                  75                  80

Cys Lys Tyr Val Ala Glu Pro Val Met Ala Gln Ser Thr Gln Asn Val
                 85                  90                  95

Asp Tyr Asn Gln
            100
```

<210> SEQ ID NO 10
<211> LENGTH: 98
<212> TYPE: PRT
<213> ORGANISM: Homo sapiens

<400> SEQUENCE: 10

```
Thr Leu Asp Leu Lys Asp Trp Lys Arg Ile Gly Lys Glu Leu Lys Gln
  1               5                  10                  15

Ala Gly Arg Lys Gly Asn Ile Ile Pro Leu Thr Val Trp Asn Asp Trp
             20                  25                  30

Ala Ile Ile Lys Ala Ala Leu Glu Pro Phe Gln Thr Glu Glu Asp Ser
         35                  40                  45

Val Ser Val Ser Asp Ala Pro Gly Ser Cys Ile Ile Asp Cys Asn Glu
 50                  55                  60

Lys Thr Arg Lys Ser Gln Lys Glu Thr Glu Ser Leu His Cys Glu
 65                  70                  75                  80

Tyr Val Ala Glu Pro Val Met Ala Gln Ser Thr Gln Asn Val Asp Tyr
                 85                  90                  95

Asn Gln
```

<210> SEQ ID NO 11
<211> LENGTH: 98
<212> TYPE: PRT
<213> ORGANISM: Human endogenous retrovirus K

<400> SEQUENCE: 11

Thr Leu Asp Leu Lys Asp Trp Lys Arg Ile Gly Lys Glu Leu Lys Gln

```
                1               5                    10                       15
         Ala Gly Arg Lys Gly Asn Ile Ile Pro Leu Thr Val Trp Asn Asp Trp
                        20                  25                  30

Ala Ile Ile Lys Ala Ala Leu Glu Pro Phe Gln Thr Glu Glu Asp Ser
                    35                  40                  45

Val Ser Val Ser Asp Ala Pro Gly Ser Cys Leu Ile Asp Cys Asn Glu
                50                  55                  60

Lys Thr Arg Lys Lys Ser Gln Lys Glu Thr Glu Ser Leu His Cys Glu
         65                  70                  75                  80

Tyr Val Ala Glu Pro Val Met Ala Gln Ser Thr Gln Asn Val Asp Tyr
                            85                  90                  95

Asn Gln

<210> SEQ ID NO 12
         <211> LENGTH: 304
         <212> TYPE: DNA
         <213> ORGANISM: Mantle histiocyte retrovirus (UV)

<400> SEQUENCE: 12
agatctaaaa gaagactgga aaagaattgg caaggaacta aagcaggtag gaagggtaat       60
atcattccac ttacagtatg gaatgattgg gccattatta aagcagcttt agaaccattt      120
caaagagaag aagatagtgt ttcagtttct gatgcccctg gaagctgtgt aatagattgt      180
aaagacaaga cagggaaaaa atcccagaaa gaaacggaaa gtttacattg caaatatgta      240
gcagagccag taatggctca gtcaacgcaa atgttgact ataatcaatc aattacaggg       300
gttg                                                                   304

<210> SEQ ID NO 13
         <211> LENGTH: 304
         <212> TYPE: DNA
         <213> ORGANISM: Mantle histiocyte retrovirus (S92-4336)

<400> SEQUENCE: 13
agatctaaaa gaagactgga aaagaattgg caaggaacta aagcaggtag gaagggtaat       60
atcattccac ttacagtatg gaatgattag gccattatta aagcagcttt agaaccattt      120
caaagagaag aagatagtgt ttcagtttct gatgcccctg gaagctgtgt aatagattgt      180
aaagacaaga cagggaaaaa atcccagaaa gaaacggaaa gtttacattg cgaatatgta      240
gcagagccag taatggctca gtcaacgcaa atgttgact ataatcaatc aattacaggg       300
gttg                                                                   304

<210> SEQ ID NO 14
         <211> LENGTH: 304
         <212> TYPE: DNA
         <213> ORGANISM: Mantle histiocyte retrovirus (Braggs)

<400> SEQUENCE: 14
agatctaaaa gaagactgga aaagaattgg caaggaacta aagcaggtag gaagggtaat       60
atcattccac ttacagtatg gaatgattgg gccattatta aagcagcttt agaaccattt      120
caaagagaag aagatagtgt ttcagtttct gatgcccctg gaagctgcgt aatagattgt      180
aaagacaaga cagggaaaaa atcccagaaa gaaacggaaa gtttacattg cgaatatgta      240
gcagagccag taatggctca gtcaacgcaa atgttgact ataatcaatc aattacaggg       300
gttg                                                                   304
```